US011618882B2

(12) United States Patent
Demirci et al.

(10) Patent No.: US 11,618,882 B2
(45) Date of Patent: Apr. 4, 2023

(54) MICRO-FLUIDIC DEVICE FOR SELECTIVE SORTING OF HIGHLY MOTILE AND MORPHOLOGICALLY NORMAL SPERM FROM UNPROCESSED SEMEN

(71) Applicants: The Board of Trustees of the Leland Stanford Junior University, Palo Alto, CA (US); Worcester Polytechnic Institute, Worcester, MA (US)

(72) Inventors: Utkan Demirci, Stanford, CA (US); Erkan Tüzel, Natick, MA (US); James Leonard Kingsley, Worcester, MA (US); Thiruppathiraja Chinnasamy, Tamilnadu (IN)

(73) Assignees: The Board of Trustees of the Leland Stanford Junior University, Palo Alto, CA (US); Worcester Polytechnic Institute, Worcester, MA (US)

( * ) Notice: Subject to any disclaimer, the term of this patent is extended or adjusted under 35 U.S.C. 154(b) by 1290 days.

(21) Appl. No.: 16/070,368

(22) PCT Filed: Jan. 22, 2017

(86) PCT No.: PCT/US2017/014479
§ 371 (c)(1),
(2) Date: Jul. 16, 2018

(87) PCT Pub. No.: WO2017/127775
PCT Pub. Date: Jul. 27, 2017

(65) Prior Publication Data
US 2019/0024045 A1 Jan. 24, 2019

Related U.S. Application Data
(60) Provisional application No. 62/286,227, filed on Jan. 22, 2016.

(51) Int. Cl.
*B01L 3/00* (2006.01)
*C12N 5/071* (2010.01)
*C12M 1/00* (2006.01)

(52) U.S. Cl.
CPC ...... *C12N 5/0612* (2013.01); *B01L 3/502746* (2013.01); *B01L 3/502761* (2013.01);
(Continued)

(58) Field of Classification Search
CPC ............ C12N 5/0612; B01L 3/502746; B01L 3/502761; B01L 2200/027; B01L 2200/0652; B01L 2300/0832; C12M 47/04
See application file for complete search history.

(56) References Cited

U.S. PATENT DOCUMENTS

| 5,296,375 A | 3/1994 | Kricka |
| 2008/0233607 A1* | 9/2008 | Yu .......................... C12M 23/34 435/299.1 |

(Continued)

FOREIGN PATENT DOCUMENTS

WO WO2015077333 5/2015

OTHER PUBLICATIONS

Bhagat et al., "Microfluidics for cell separation", Med Biol Eng Comput48: 999-1014, published online Apr. 23, 2010. (Year: 2010).*
(Continued)

Primary Examiner — Rebecca M Giere
(74) Attorney, Agent, or Firm — Quarles & Brady LLP

(57) ABSTRACT

A microfluidic chip is provided for self-sorting highly motile, morphologically normal sperm cell with high DNA integrity from a fresh semen sample. The sperm self-sorting microfluidic chip has one or more inlet chambers, and sperm collection outlet chamber(s), and the middle of the channel features various micro-fabricated structures in different geo-
(Continued)

metrical shapes and orientations, with varying periodicities and patterns, such as an array of micro-fabricated pillars that facilitate the transport of the active and healthy sperm into the outlet chamber.

10 Claims, 33 Drawing Sheets

(52) U.S. Cl.
CPC . *B01L 2200/027* (2013.01); *B01L 2200/0652* (2013.01); *B01L 2300/0832* (2013.01); *C12M 47/04* (2013.01)

(56) References Cited

U.S. PATENT DOCUMENTS

| | | |
|---|---|---|
| 2011/0081674 A1 | 4/2011 | Han |
| 2011/0287948 A1 | 11/2011 | Suresh |
| 2013/0079251 A1 | 3/2013 | Boles |
| 2014/0030788 A1 | 1/2014 | Chen |
| 2015/0140655 A1 | 5/2015 | Nosrati |

OTHER PUBLICATIONS

Tung et al., Cooperative roles of biological flow and surface topography in guiding sperm migration revealed by microfluidic model, Lab Chip, 2014, 14, pp. 1348-1356. (Year: 2014).*
Karaback et al. Microfluidic, marker-free isolation of circulating tumor cells from blood samples Natura protocols, vol. 9, No. 3, 2014, p. 694-710.
Cho et al. Passively Driven Integrated Microfluidic System for Seperation of Motile Sperm. Anal. Chem. 2003, 75: 1671-1675.
Loutherback. Microfluidic Devices for High Throughput Cell Sorting and Chemical Treatment. http://dataspace.princeton.edu/jspui/bitstream/88435/...dsp01cv43nw82k/1/Louterhback_0181D_10043.pdf (Internet citation).
Nosrati et al. Rapid selection of sperm with high DNA integrity. Lab on Chip (2014) vol. 14, pp. 1142-1150.

* cited by examiner

| Solvent Parameters | |
|---|---|
| Parameter | Value |
| Width | 156 |
| Height | 132 |
| $a$ | 1 |
| $k_B T$ | 1 |
| $\tau$ | 0.025 |
| $\tau_{MD}$ | 0.00025 |
| $\alpha$ | $\pi/2$ |
| $m$ | 1 |
| $\rho$ | $10/a^2$ |
| discarded equilibration time | 10 |
| run time | 50000 |

| Sperm Parameters | |
|---|---|
| Parameter | Value |
| $k_{\text{spring}}$ | 1000000 |
| $k_{\text{bend}}$ | 3000 |
| $A$ | 1.0 |
| $\omega$ | $0.05\pi$ |
| $k$ | 0.2 |
| particle mass | 10 |
| head diameter | 5 |
| neck length | 4 |
| tail length | 50 |
| position recording frequency | $1/10\tau$ |

| Post Parameters | |
|---|---|
| Parameter | Value |
| point-to-point spacing | 1 |
| particle mass | 5 |
| post radius (to particle center) | 3.6 |
| spacing (x) | 26 |
| spacing (y) | 22 |
| Lennard-Jones $\epsilon$ | 50 |
| Lennard-Jones $\sigma$ | 1.0 |

FIG. 30

$$\rho(\mathbf{R},d,t-\tau/2) = \sum_i P(i,d)\rho(\mathbf{R}-i,d,t-\tau) + \left(1 - \sum_i P(i,d)\right)\rho(\mathbf{R},d,t-\tau)$$

$$\rho(\mathbf{R},d,t) = \sum_e Q(d,e)\rho(\mathbf{R},e,t-\tau/2)$$

FIG. 31

MICRO-FLUIDIC DEVICE FOR SELECTIVE SORTING OF HIGHLY MOTILE AND MORPHOLOGICALLY NORMAL SPERM FROM UNPROCESSED SEMEN

CROSS-REFERENCE TO RELATED APPLICATIONS

This application is a 371 of PCT application PCT/US2017/014479 filed Jan. 22, 2017. PCT application PCT/US2017/014479 claims the benefit of U.S. Provisional application 62/286,227 filed Jan. 22, 2016.

STATEMENT OF GOVERNMENT SPONSORED SUPPORT

This invention was made with Government support under contract 1464673 awarded by the National Science Foundation. The Government has certain rights in the invention.

FIELD OF THE INVENTION

This invention relates to methods, devices, and systems for sorting highly motile, morphologically normal, and/or genetically normal sperm from unprocessed semen.

BACKGROUND OF THE INVENTION

Human infertility is a worldwide disease of epidemic proportions, with an estimate of 80 million couples affected annually. In developed countries, 1-3% of all births are conceived via assisted reproduction, most commonly in vitro fertilization (IVF) and intracytoplasmic sperm injection (ICSI) [1]. Among infertility causes, one third are of male origin and many such cases are treated with assisted reproduction (ART) [2, 3]. Although powerful enough to bypass human infertility, assisted reproductive techniques commonly fail to do so, with live birth rates averaging less than 35% per cycle in the U.S. in 2014 [4]. In addition, ART may have associated risks to offspring which include: (a) increased risk of sex chromosome anomalies, (b) increased risk of genomic imprinting disorders [5, 6], (c) a controversial increased risk of birth defects, and (d) transmission of paternal or maternal infertility issues [7]. Although helpful to many couples, ART is still limited in its ability to overcome most of human infertility.

When ART is used for male-factor infertility, sperm are usually processed with traditional gradient wash or swim-up techniques to enhance for motile and morphologically normal sperm [8-10]. With ICSI, sperm are then selected for use by trained embryologists who chose individual sperm for egg injection based on morphological features [7, 11]. Other sperm attributes that can affect ART outcomes such as embryo quality, pregnancy and miscarriage rates, include sperm DNA-chromatin, or chromosomal integrity or mutational or methylome analyses, and these are not considered in routine ICSI procedures [12-13]. This begs the question of whether or not important and consequential natural selection barriers to sperm are being bypassed by the ICSI technique.

Currently, there are no reliable ways to non-invasively assess sperm attributes that might be particularly relevant to successful conception and birth when employing ICSI. These shortcomings in the art are addressed by the present invention.

SUMMARY OF THE INVENTION

The present invention provides a method and device for self-sorting relatively high-motile or morphologically-normal sperm cells with high DNA integrity from raw or unprocessed semen.

In one embodiment, the invention provides a fluidic channel with an inlet at one end and an outlet at the other end. An array of pillar-structures is periodically spaced inside the fluidic channel. The spacing between adjacent pillar-structures ranges from one micrometer to 250 of micrometers. Raw or unprocessed semen containing sperm cells is inducted at the inlet of the fluidic channel. At the outlet sorted sperm cells is collected from the fluidic channel. The sorted sperm cells have being self-sorted by their own self-induced movements within the fluidic channel though their interactions with the periodically spaced array of pillar-structures, wherein the device and the self-sorting operates without the use of any external flow, forces or mechanisms to feed the raw or unprocessed sperm through the fluidic channel, and wherein the self-sorting outputs in the outlet the relatively highly-motile, morphologically normal sperm cells with high DNA integrity compared to the non-sorted sperm unprocessed semen.

In another embodiment, the invention provides a fluid channel with one or more inlets for the induction of raw sperm into the device, and one or more arrays of geometric structures or impediments periodically spaced inside the fluidic channel. The spacing between adjacent pillar-structures ranges from one micrometer to five hundred micrometers.

The array of geometric structures is designed such that when the self-induced movements of sperm occur within the array, the sperm self-sort without the use of any external flow, forces or mechanisms to feed the raw or unprocessed sperm through the fluidic channel. These geometric structures could be cylindrical, square, hexagonal, or other types of prisms, and could be bare or coated with any type of chemicals that attract or repel sperm cells. The array of structures could be square, rectangular, hexagonal or any other tessellating pattern.

The sorting process selects the relatively highly-motile, morphologically-normal, or genetically-normal sperm cells compared to the non-self-sorted sperm cells. One or more outlets are used for the collection of sorted sperm from the device.

The arrangement of the inlet(s), pillar array(s), and outlet(s) could be a line, circle, or other arrangement.

In still another embodiment a method of self-sorting sperm cells is provided using a device as described supra. A sperm sample is inserted, whether raw or otherwise processed, into the inlet of the device. The device is incubated for a period of time ranging from five to sixty minutes. During this incubation process, the sperm cells undergo a self-sorting process without the use of any external flow, forces or mechanisms beyond the initial deposition to feed the unprocessed sperm through the fluidic channel, and whereby the self-sorting outputs the relatively highly-motile, morphologically-normal, high DNA integrity and low epigenetic abnormality sperm cells compared to the unprocessed semen.

A portion of the sperm is extracted from the outlet of the device. Those sperm cells being primarily the ones with a preferred quality selected for by the device, such as having (i) high-motility and linear persistence, (ii) morphological-normality, (iii) high DNA integrity, and (iv) low epigenetic abnormality. The un-extracted sperm is discarded, which is the sperm being the less preferred in comparison to the ones in the outlet.

BRIEF DESCRIPTION OF THE DRAWINGS

FIG. 30 shows according to an exemplary embodiment of the invention parameters chosen for the SRD simulation of sperm.

FIG. 31 shows according to an exemplary embodiment of the invention the equations that describe the coarse-grained simulation of the device and method.

DETAILED DESCRIPTION

For the purposes of the present invention, the sperm journey through the female reproductive tract, a phenomenon conserved in viviparous mammals throughout millions of years of evolution and reproduction, is argued to be a naturally effective "filter" for fertile sperm. The physical components of this pathway are mimicked in vitro using a microfluidic approach, designed via multi-scale computer simulations that incorporate the fluid physics, and examined how this artificial cervical-uterine-fallopian tube pathway influences the descriptive characteristics of sperm, as well as more subtle, but clinically relevant measures of fertile sperm, including DNA integrity and methylome status.

The developed SPARTAN (Simple Periodic ARray for Trapping And isolatioN) method successfully mimics the fundamental filtering characteristics of the natural pathway and isolates highly motile and morphologically normal sperm with high DNA integrity and low epigenetic aberrance for use in the fertility clinic.

Figure 1:
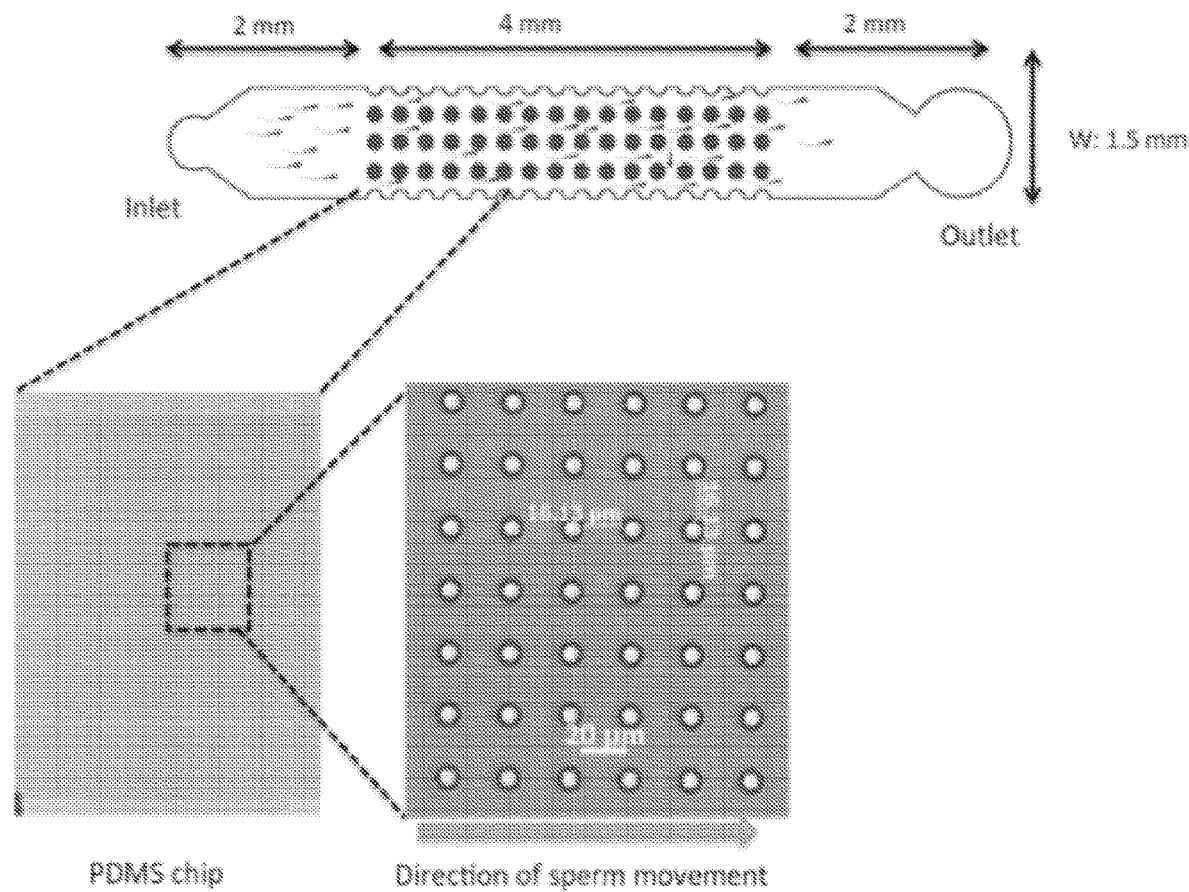
FIG. 1 shows according to an exemplary embodiment of the invention a schematic of a microfluidic sperm-sorting chip with periodic structures. The sample PDMS chip design shown is bonded on to a glass substrate, with a channel width of 1.5 mm, length 8 mm and height 50 μm. In the middle of the channel, cylindrical structures (of 10 μm diameter in this figure) form a periodic array.

The device to enable this method features series of micro-fabricated structures, to optimize the self-sorting efficiency and the selection of morphologically viable sperm. A schematic of the microfluidic device is shown in FIG. 1. At one part of the device, an inlet, or a set of inlets are formed by holes through the upper surface of the device. This is optionally followed by a transition area of the microchannel that does not contain any surface features. The transition area is not required for the functioning of the device, but may be required for practical fabrication. The next part of the device is the primary active region, consisting of a regular array of pillars. One example of the geometry that this array could take is a rectangular lattice of cylinders. After the periodic structure array, there is a second optional transition area, followed by an outlet, or set of outlets, again formed by holes through the upper surface of the device.

The device is used by first filling it with a buffer solution that can support sperm cells. One example of this solution would be sperm washing medium.

Additionally, to prevent medium evaporation, the inlet(s) and outlet(s) can be covered by a non-evaporating medium that is immiscible in the buffer solution. One example of such a medium is mineral oil. The device is then loaded by depositing a raw sperm sample into the inlet(s), via a method such as a pipette. The device is then incubated for a prescribed period of time, ranging from 5 to 120 minutes depending on the device. At this point, the sorted sperm can be collected from the outlet(s), again using a method such as a pipette.

Figure 2:
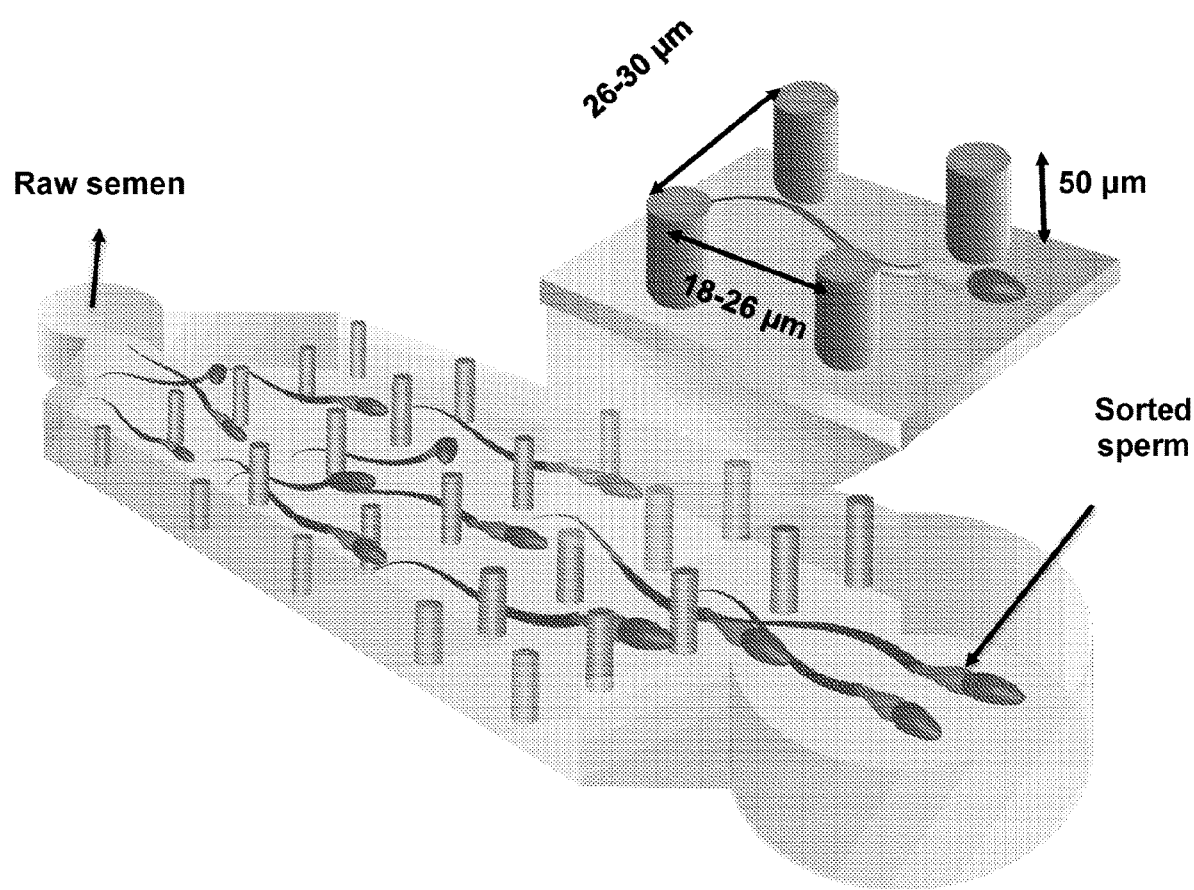
FIG. 2 shows according to an exemplary embodiment of the invention the Simple Periodic ARray for Trapping And isolatioN (SPARTAN) method for selecting motile and morphologically normal sperm. Spacing values are given for illustration purposes only.
Figure 3:
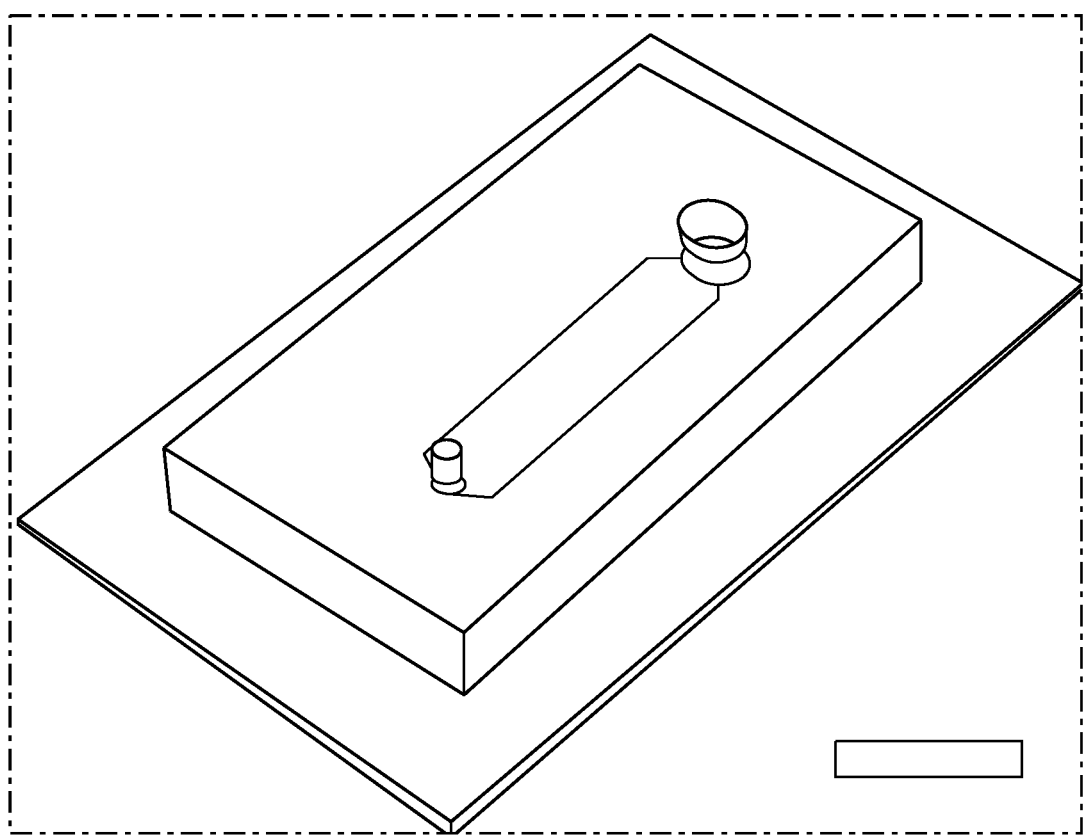
FIG. 3 shows a photograph of an exemplary embodiment of the microfluidic device (scale bar 10 mm).
Figure 4:
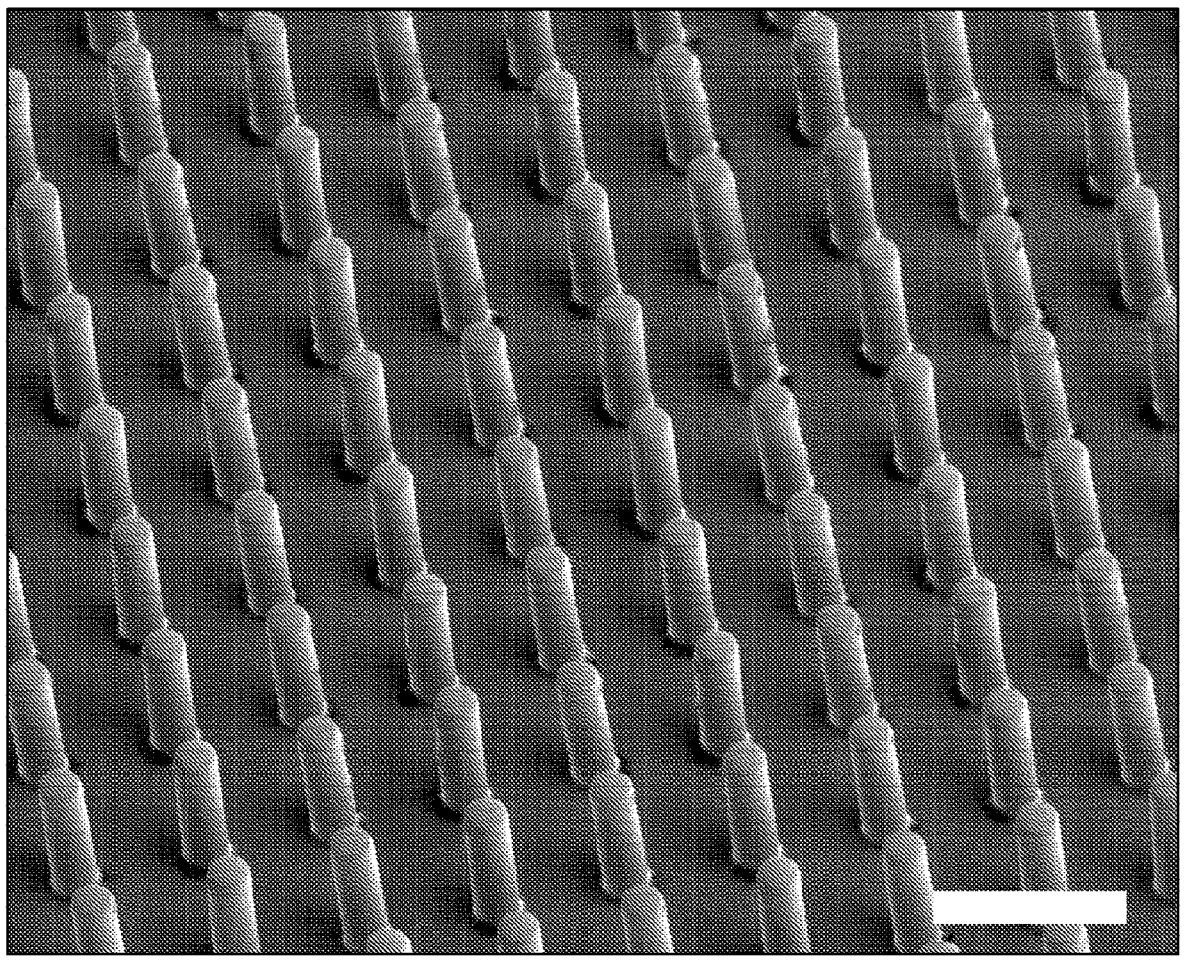
FIG. 4 shows an SEM image of an exemplary embodiment of a periodic structure array in the device (scale bar 50 μm).
Figure 5:
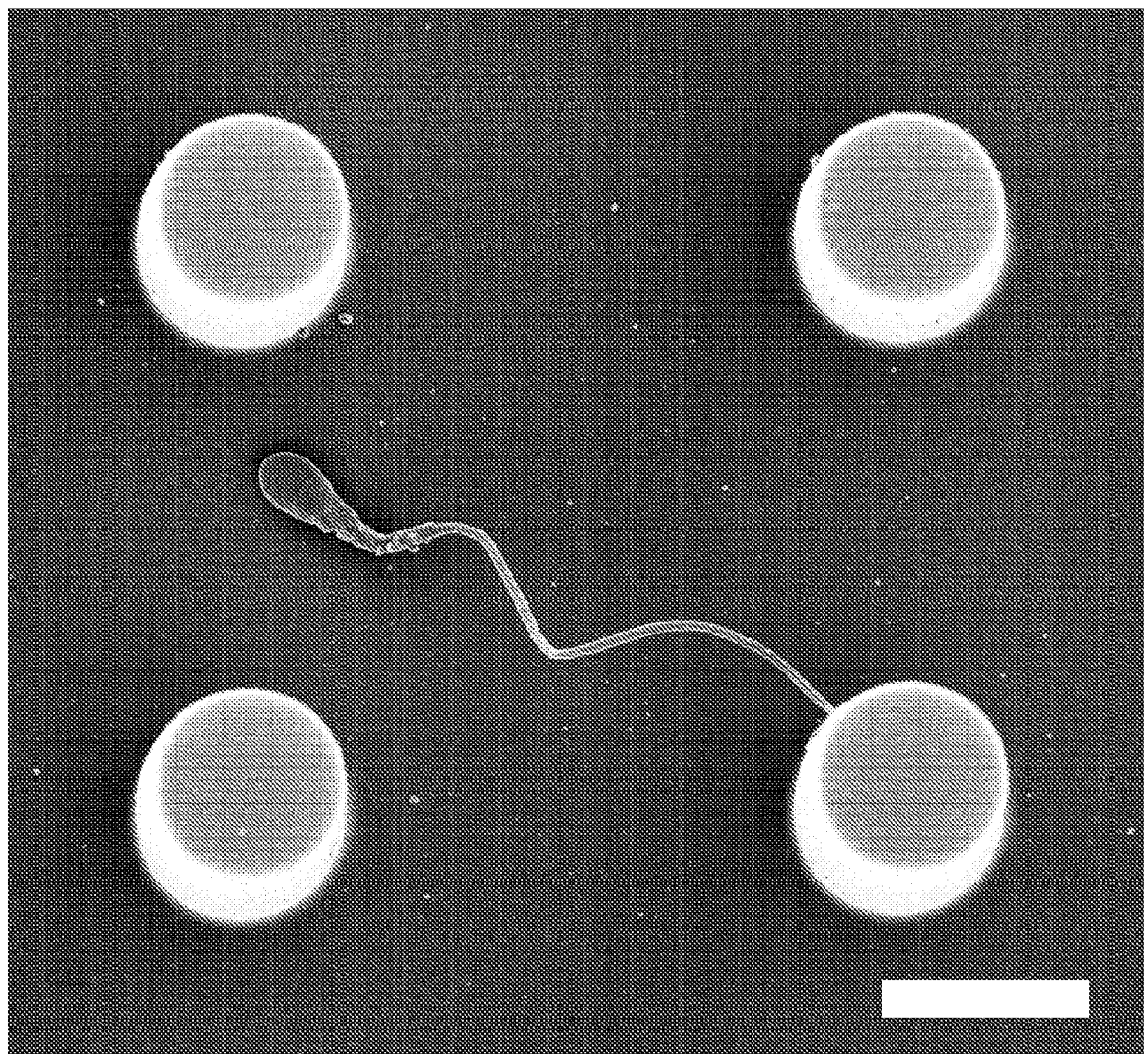
FIG. 5 shows an FESEM image of an exemplary embodiment of the periodic pillar array with a sperm cell in it (scale bar 20 μm).

For proof of concept, an example microfluidic sperm-sorting device with cylindrical structures was fabricated using standard soft lithography. In brief, a 50 micrometer thickness layer of SU-8 photoresist was coated and developed on a 4" silicon wafer, creating a micro-channel. Subsequently, sperm sorting microfluidic chip was fabricated using Sylgard 184 (Dow Corning, Midland, Mich., USA) in a 1:10 v/v ratio of base versus curing agent that was poured onto silicon wafer, degassed, and cured at 70 degrees Celsius for 2 hours. After curing, the inlet and outlet chambers were punched using Acu Punch (tips 1.0 and 2.0 mm). The resulting channel was sealed on a glass slide using oxygen plasma, and baked at 60 degrees Celsius for 30 minutes before use. A schematic of this specific device is shown in FIG. 2, and a photograph of the actual device is shown in FIG. 3. An FESEM image of the micro-fabricated period structures is shown in FIG. 4, and a sperm cell inside this structure in shown in FIG. 5.

The purpose of the present device is to sort motile and healthy sperm cells in an efficient way, taking advantage of the hydrodynamic effects induced by the periodic structures in the microfluidic channel on the sperm cells. As there are many variables involved, such as periodic structure dimensions and shape, the spacing between structure elements, channel length, collection time, etc., a multi-scale computational model was developed to optimize channel design.

Device Design Using Multi-Scale Computer Modeling Approach

Figure 6:
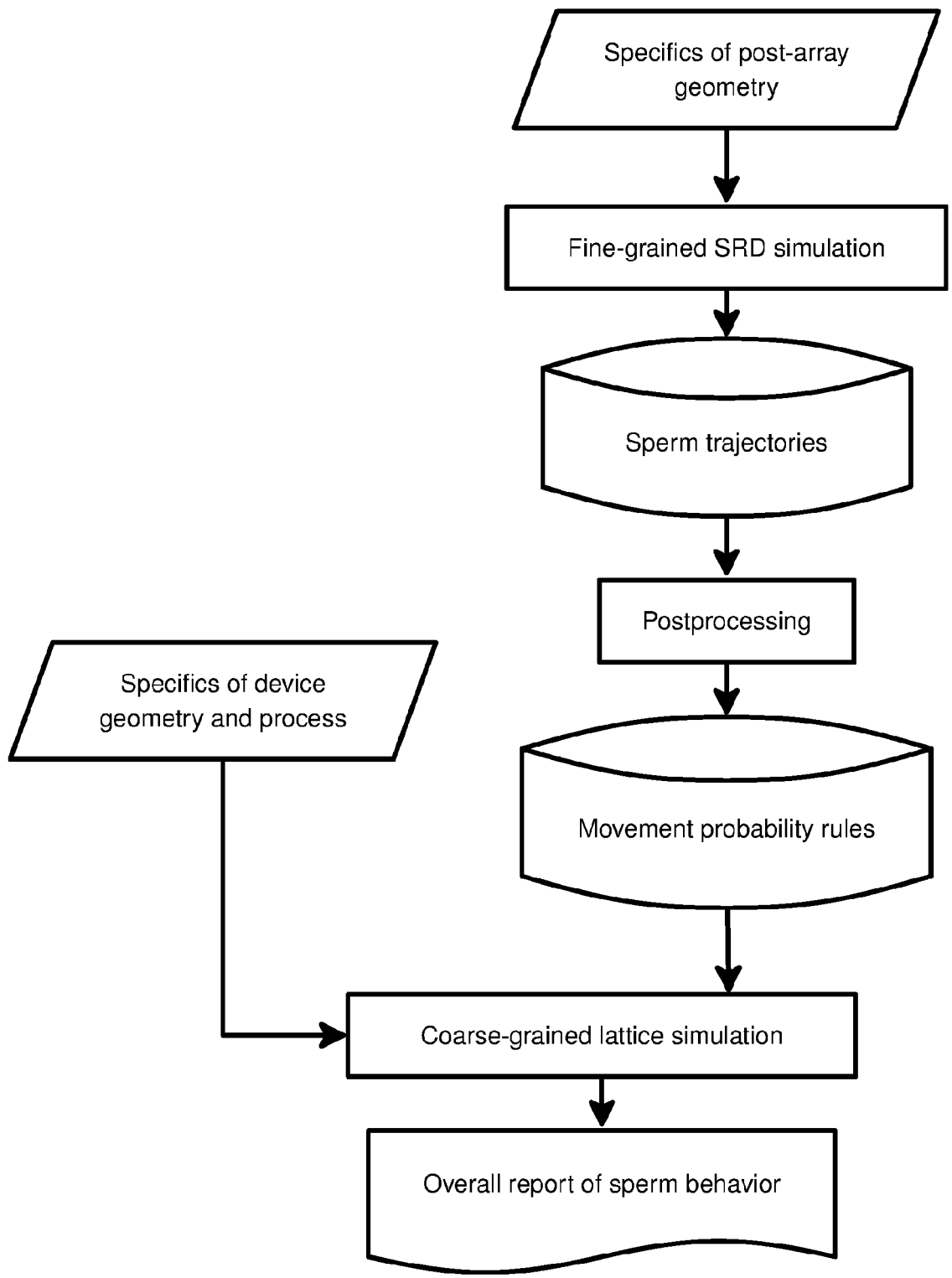
FIG. 6 shows according to an exemplary embodiment of the invention a flow chart outlining the process used to run simulations to design some exemplary embodiments of the device.

Since it is not clear or obvious how the geometric features of the self-sorting device can be chosen due to the non-linear nature of the fluid-swimmer coupling and the presence of complex geometries, we created a multi-scale model to simulate the movement of sperm cells in the device. The model is composed of two pieces: a fine-grained particle-based model, and a coarse-grained model using probabilistic movement along the lattice formed by the periodic array. Briefly, the fine-grained model uses Stochastic Rotation Dynamics (SRD), a particle-based mesoscale solvent that has been successfully used on numerous soft-matter systems for over a decade. In SRD, the fluid is modeled in a coarse-grained fashion, the sperm cells are embedded as bead-and-spring structures, and the pillars as impenetrable barriers, all of which interact via hydrodynamic interactions in the presence of thermal fluctuations. This model produces microscopic trajectories, which are then used to train a probabilistic, rule-based lattice model to describe the sperm's movement in a given pillar geometry for realistic time and length scales. More specifically, the coarse-grained model is a discrete-time lattice model with rotation. At each time-step, the sperm has a direction-dependent probability of rotating right or left, followed by a probability of taking a step along the lattice. By loading the probability rules produced from the SRD model, this model can replicate the sperm's behavior for a large number of sperm and many steps. Overview of the modeling approach is shown in FIG. 6. For further details, see infra the section on Details of the Modeling Approach.

Simulation Results on Speed and Collection Rate

Figure 7:
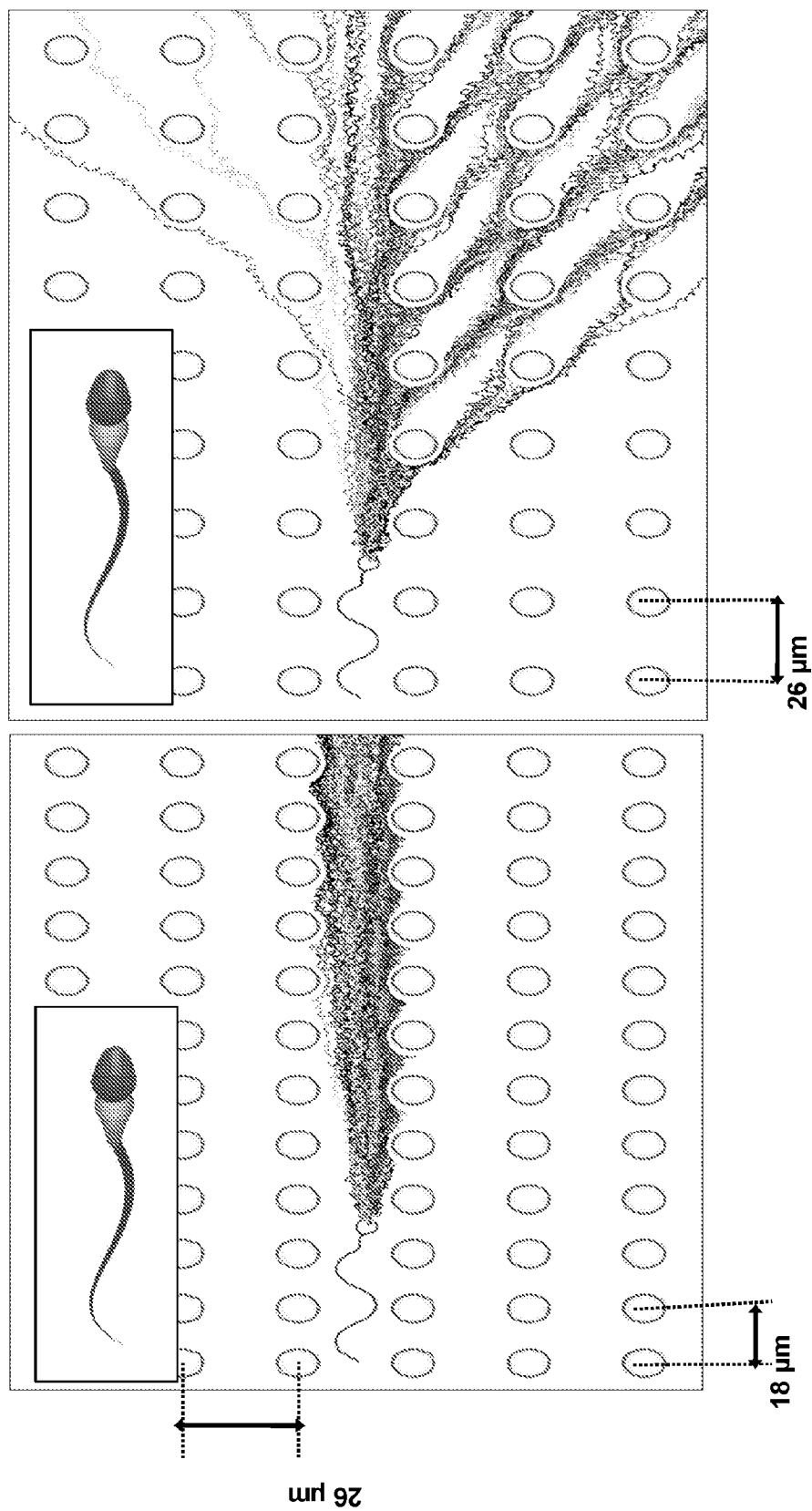
FIG. 7 shows according to an exemplary embodiment of the invention simulated trajectories of (n=100) normal sperm in exemplary channels with 18×26 μm (left) and 26×26 μm (right) structure array geometries.

Several simulation geometries were constructed to investigate the effects of periodic set of obstacles have on the behavior of sperm using our multi-scale model. Since sperm are known to have hydrodynamic interactions with surfaces in their vicinity, one plausible outcome of such interactions is that various arrangements could speed up, slow down, or redirect incident sperm. Our simulations showed behaviors where at sufficiently small pillar spacing, sperm would get stuck due to the rigidity of the simulated sperm. Once above this tight confinement, however we found that sperm would hold quite persistent trajectories in the geometry (see FIG. 7).

In addition, if the grid had a small aspect ratio in one dimension and a large aspect ratio in the other (on the order of the length of the sperm), the sperm would preferentially swim along the long-spacing axis. This effect is, on its face, paradoxical, as one would naively expect that sperm would take the path of least resistance—i.e. the wide channels. However, when the pillars are fairly close together, they act somewhat like a porous wall, and the sperm is attracted to them. Like all pusher swimmers, the swimming geometry of sperm causes them to turn towards the surface they swim against. When interacting with a flat surface, this causes the sperm to follow it. However, when the surface has gaps of sufficient size and favorable geometry, the sperm will turn into and swim through the gap. The net effect is redirecting of the sperm.

Having the option to redirect sperm allows us to give a path along which the active swimmers (healthy sperm) will preferentially travel, while debris and dead sperm will be limited by diffusion. This will allow us to make significantly smaller and faster devices for separation and selection of healthy sperm.

Simulation Results on Morphological Selection

Figure 8:
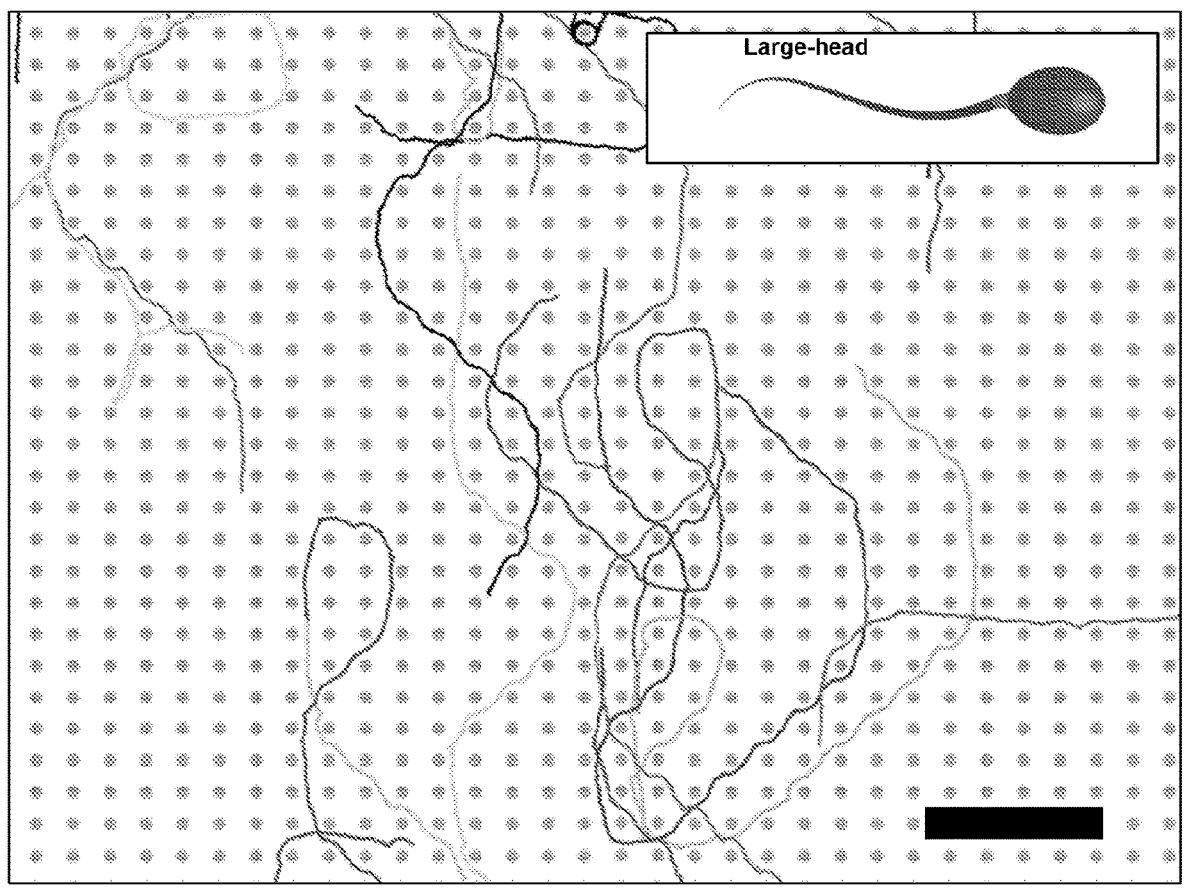
FIG. 8 shows according to an exemplary embodiment of the invention simulated trajectories of (n=100) sperm with abnormal morphology (3× larger heads) in a channel with a 30×26 μm structure array geometry.
Figure 9:
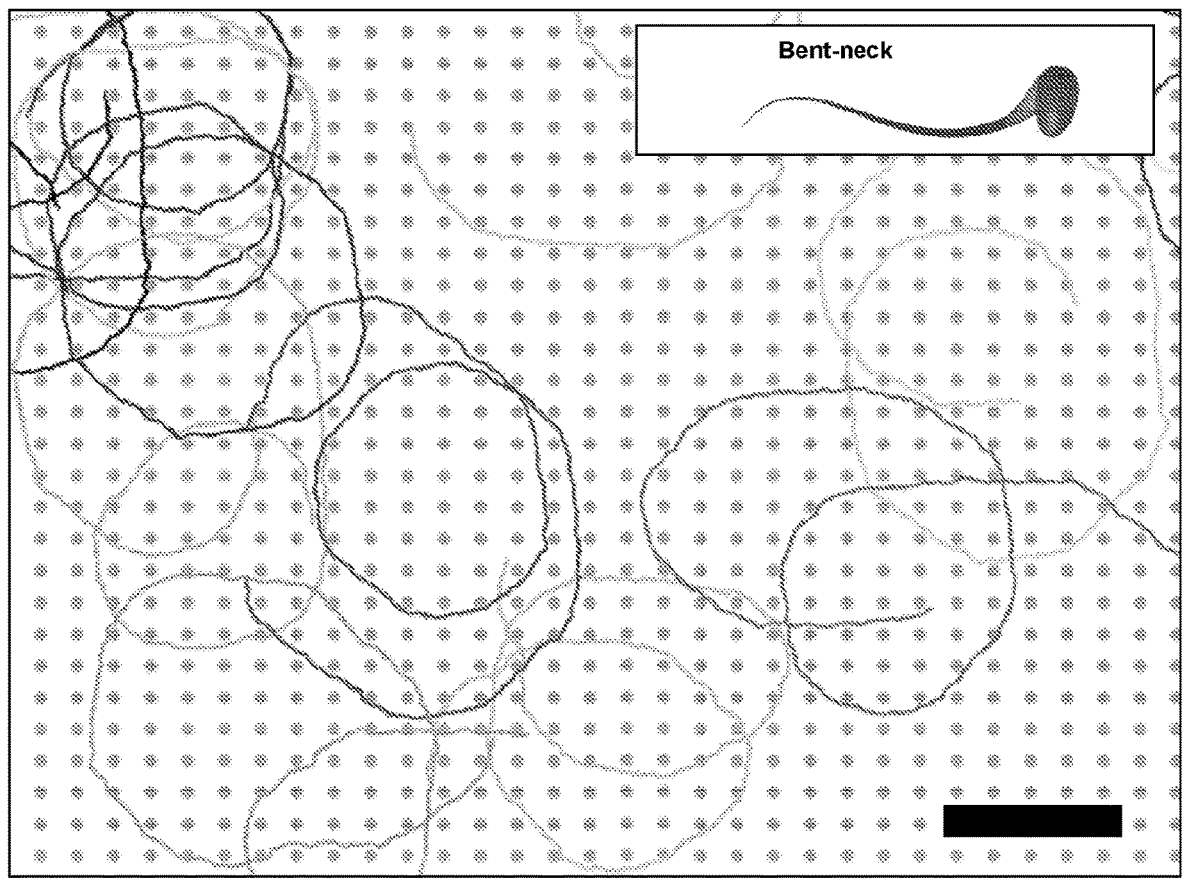
FIG. 9 shows according to an exemplary embodiment of the invention simulated trajectories of (n=100) sperm with abnormal morphology (18 degree bent necks) in a channel with a 30>26 μm structure array geometry.

We additionally studied the differential effects of the pillar geometries on sperm with morphological defects. Sample simulated trajectories of sperm with a bent-neck and ×2 larger head are shown in FIGS. 8 and 9. As both of these cases illustrate, we find that the periodic geometric impediments encourage the turning behavior of the sperm and thus confine them more effectively than a simple channel.

Experimental Results

Using the predictions from the simulations as a guide, we fabricated a proof-of-concept sample micro-fluidic channel featuring high aspect ratio cylindrical periodic arrays. More specifically, the dimensions of the microfluidic chip fabricated are 8 mm in length and 1.5 mm in width with 1 mm and 2 mm inlet and outlet chamber diameters, respectively. In the middle of the channel, 10 μm in diameter cylindrical structures are placed at a specific distance to each other.

Sperm sorting analysis was performed using a de-identified discarded semen sample from IVF Laboratory, Stanford School of Medicine. Initially, the sperm-sorting microfluidic chip was pre-filled with sperm washing medium, and a thin layer of mineral oil was placed on top of the medium outlet to prevent medium evaporation during sperm-sorting analysis. De-identified discarded semen sample of volume 0.5-2 μL (4000-6000 sperms/μL) was added into the inlet reservoir, and then inlet was covered with a layer of mineral oil. Subsequently, the sperm sorting chip was placed in an incubator at 37° C. for 15 minutes. Finally, the sorting chip was imaged and analyzed using light microscopy (Carl Zeiss, Axio Vision 4.8.2. SP3) for percentage of motile sperm, sperm trajectory, and recovery percentage at the outlet.

Figure 10:
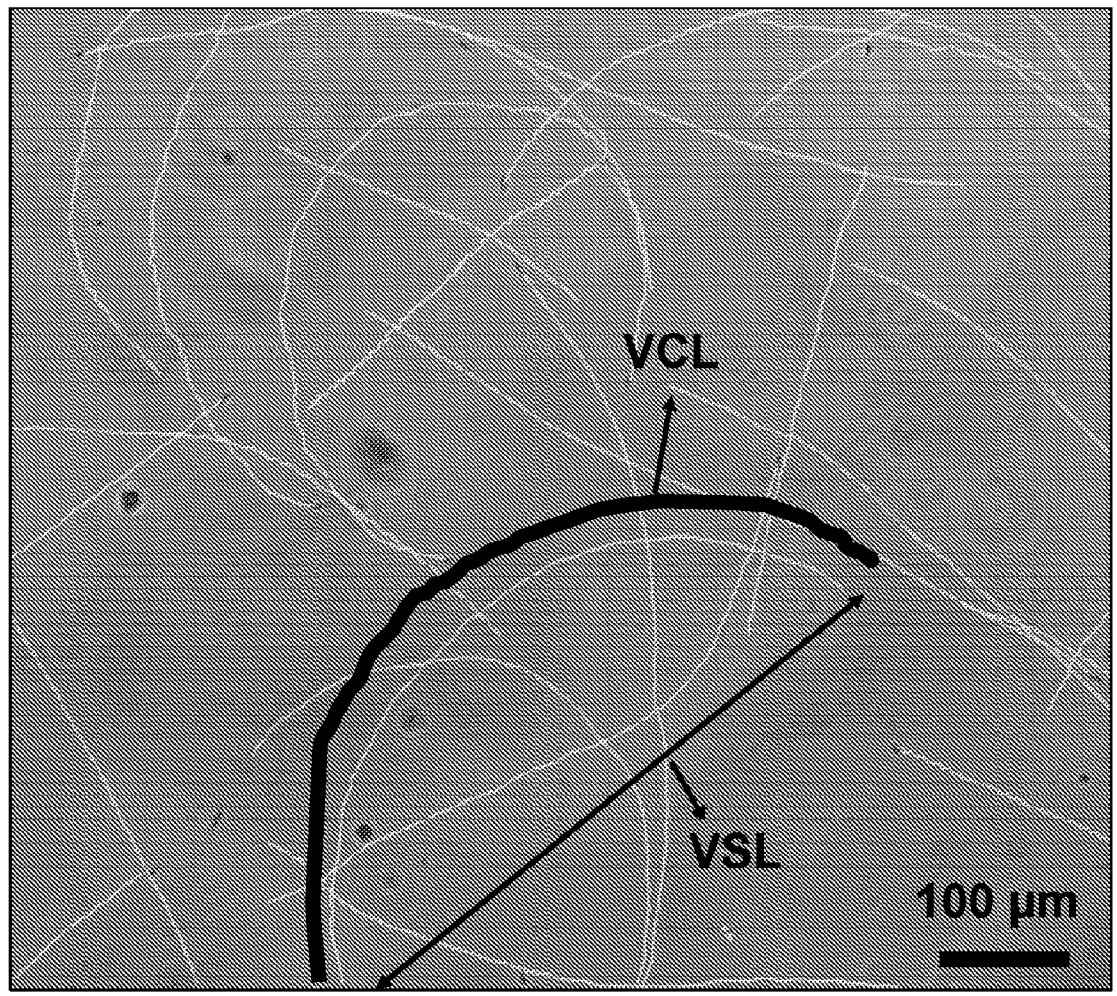
FIG. 10 shows according to an exemplary embodiment of the invention a method of measuring curvilinear and straight-line velocity.

The sperm trajectory kinematic parameters such as sperm motility, curvilinear velocity (VCL), and straight-line velocity (VSL) were measured. VCL refers to the distance that the sperm head covers during the observation time. VSL refers to the straight-line distance between the starting and the ending points of the sperm trajectory (see FIG. 10). The percentage of motile sperm was defined as the fraction of motile sperm relative to the total sperm count.

Figure 11:
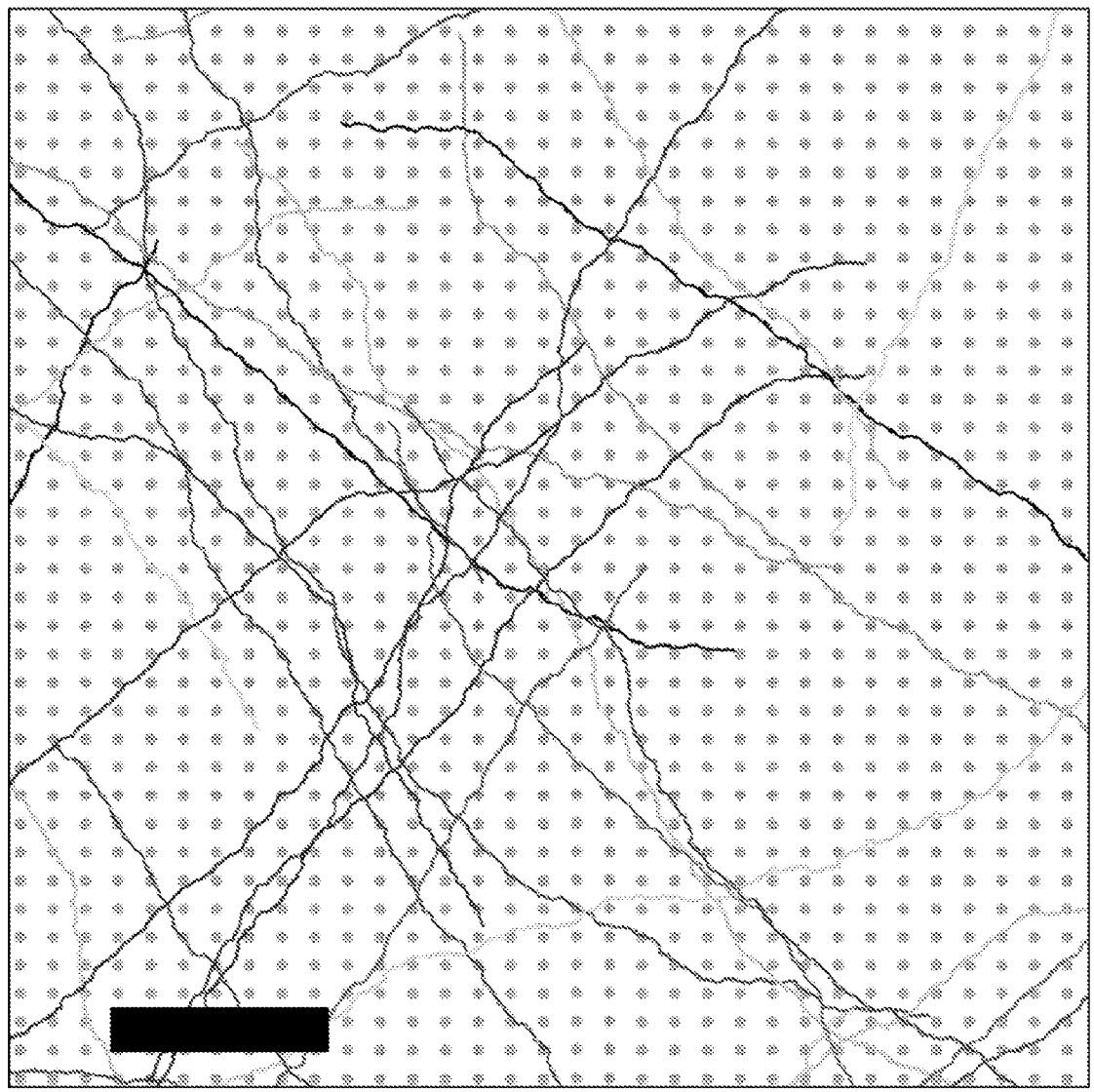
FIG. 11 shows according to an exemplary embodiment of the invention simulated trajectories of (n=100) normal sperm in an exemplary channel with a 30×26 μm structure array geometry.
Figure 12:
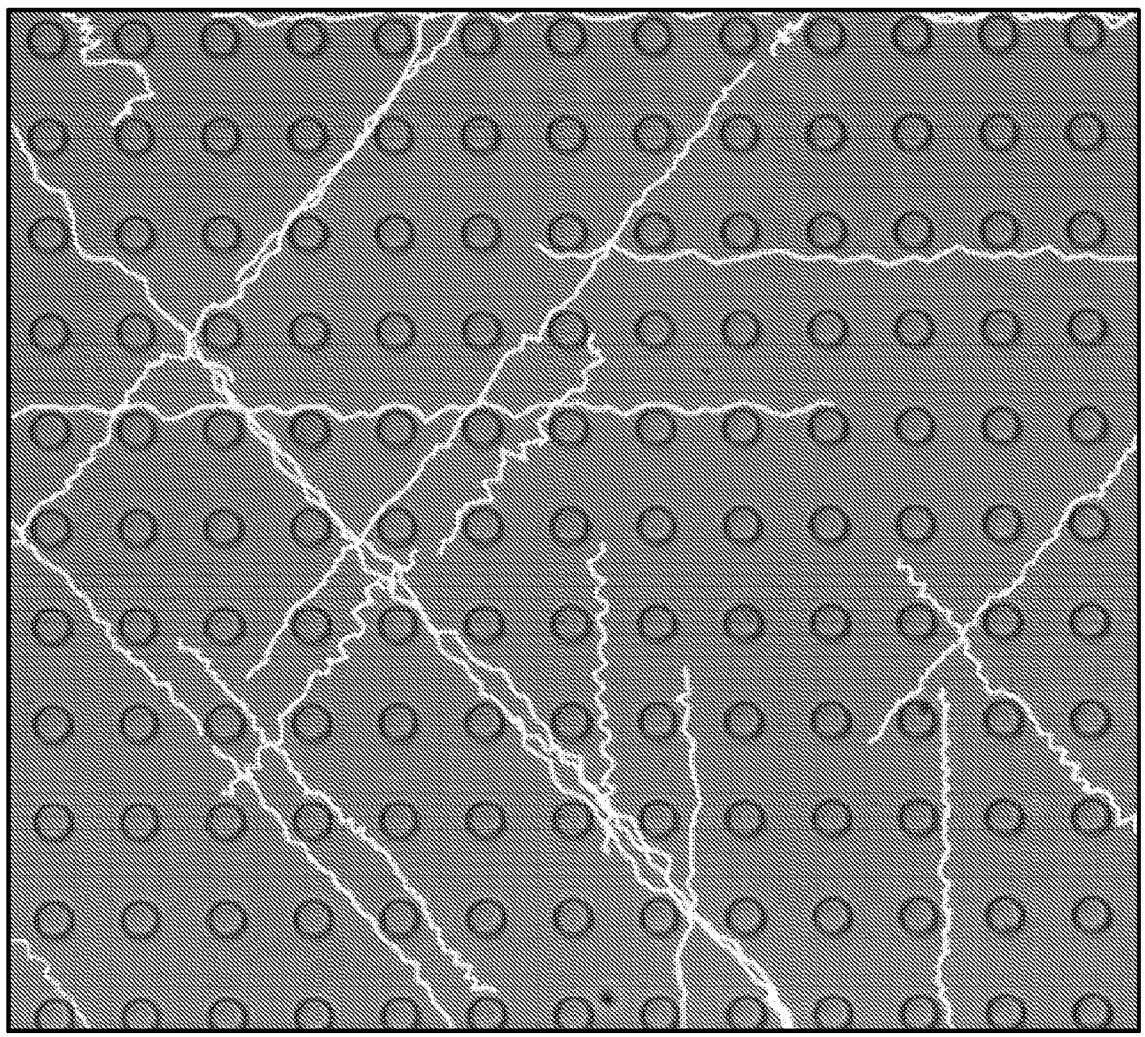
FIG. 12 shows according to an exemplary embodiment of the invention trajectories of sperm in an exemplary channel with a 30×26 μm structure array geometry.
Figure 13:
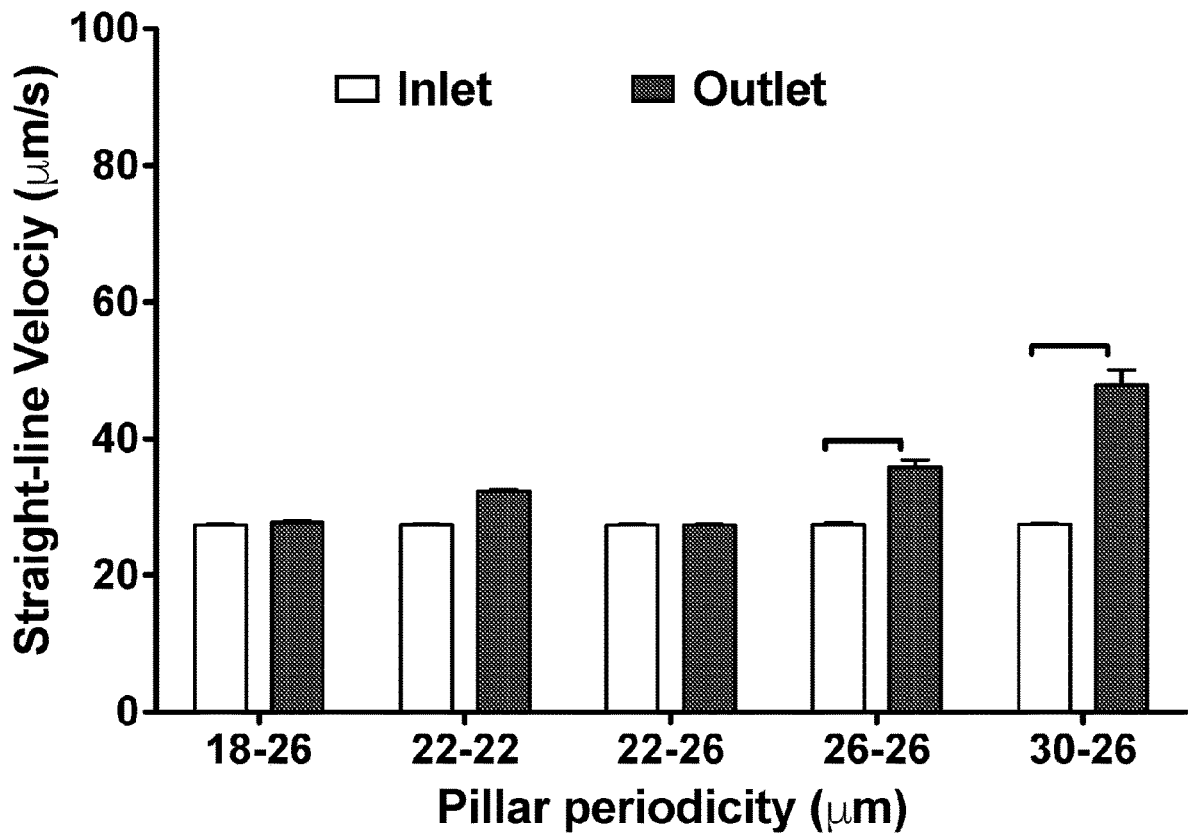
FIG. 13 shows according to an exemplary embodiment of the invention simulated results of the straight-line velocity (VSL) of sperm before and after passing through a sample of exemplary channels with various structure array geometries.
Figure 14:
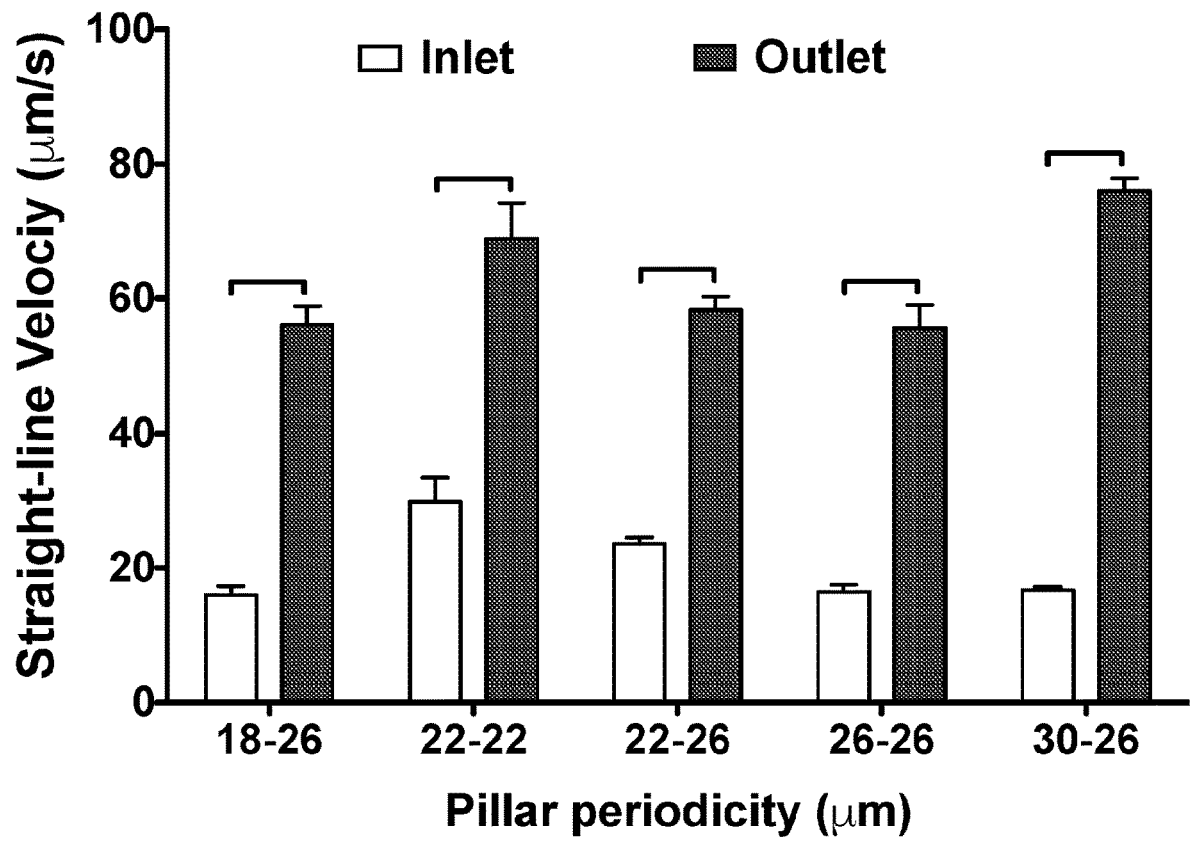
FIG. 14 shows according to an exemplary embodiment of the invention experimental results for the straight-line velocity (VSL) of sperm before and after passing through a sample of exemplary channels with different spacing values between the pillars in the array.
Figure 15:
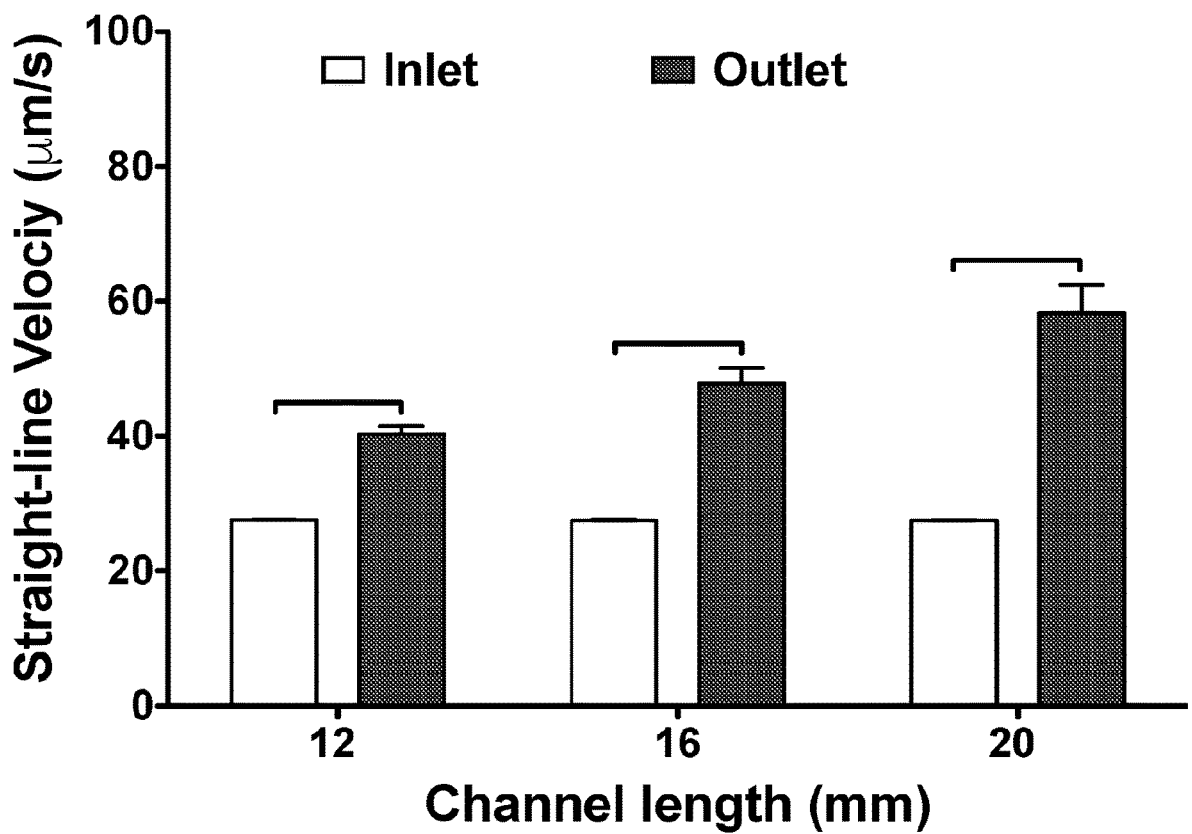
FIG. 15 shows according to an exemplary embodiment of the invention simulated results of the straight-line velocity (VSL) of sperm before and after passing through a sample of exemplary channels with various lengths.
Figure 16:
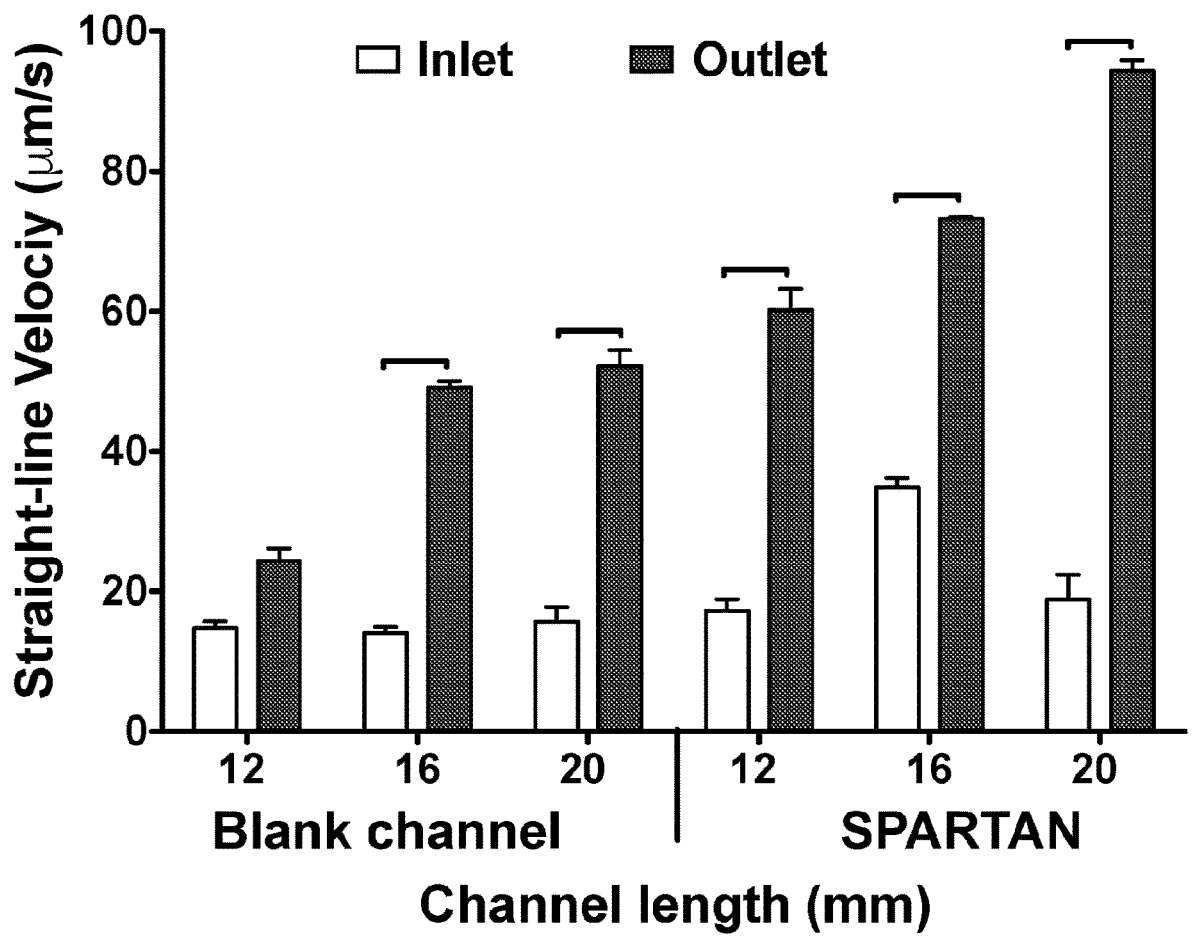
FIG. 16 shows according to an exemplary embodiment of the invention experimental results for the straight-line velocity (VSL) of sperm before and after passing through a sample of exemplary channels with various lengths.
Figure 17:
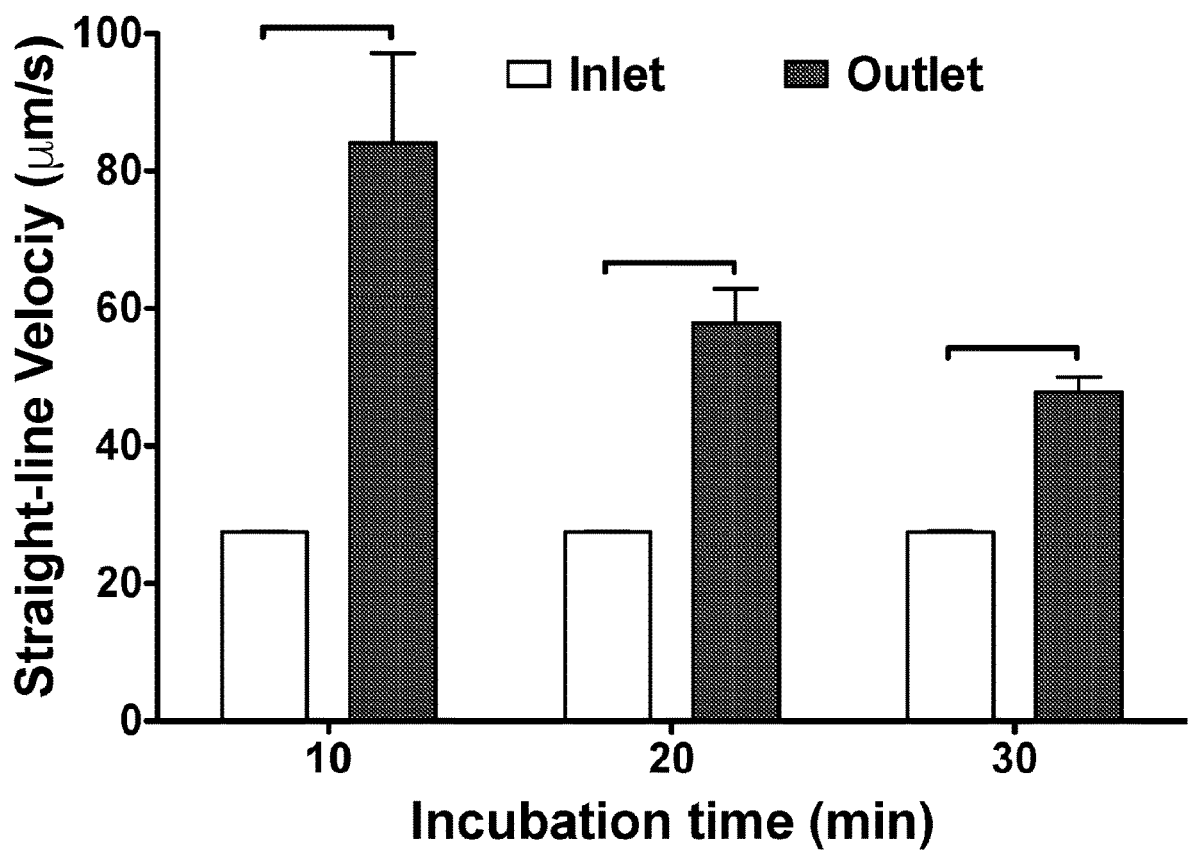
FIG. 17 shows according to an exemplary embodiment of the invention simulated results of the straight-line velocity (VSL) of sperm before and after passing through a sample of exemplary channels with various incubation times.
Figure 18:
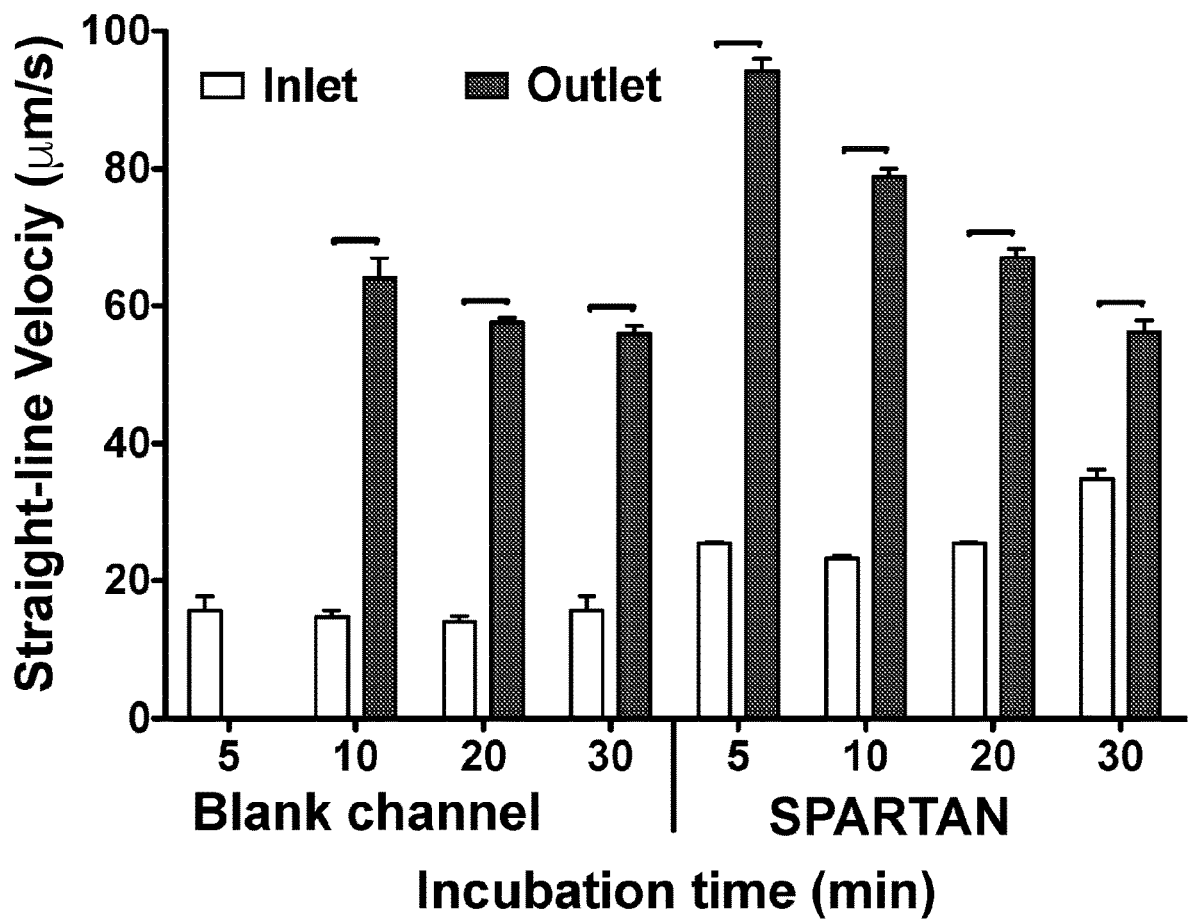
FIG. 18 shows according to an exemplary embodiment of the invention experimental results for the straight-line velocity (VSL) of sperm before and after passing through a sample of exemplary channels with various incubation times.

Our simulation and experimental results are in excellent agreement showing how the successful design parameters were obtained using computer simulations. FIGS. 11 and 12 show computer-simulated and in vitro experimental sperm trajectories for the 30×26 μm array periodicity. Straight-line velocity (VSL) values are compared at the inlet versus outlet after 30 minutes of incubation from FIG. 13, the multi-scale simulations, and FIG. 14, experiments, for different array periodicities. FIG. 15 shows straight-line velocity (VSL) values obtained from the multi-scale simulations of sperm trajectories at the inlet and outlet (after 30 min of incubation), for varying channel lengths with 30×26 μm array periodicity. FIG. 16 shows experimental measurements of VSL for channels with 30×26 μm array periodicity with varying lengths (30 min of incubation at outlet). Sperm sorting for varying incubation times at outlet compared with the blank channel is illustrated through VSL analysis for FIG. 17 simulation, and FIG. 18 experimental measurement.

Figure 19:
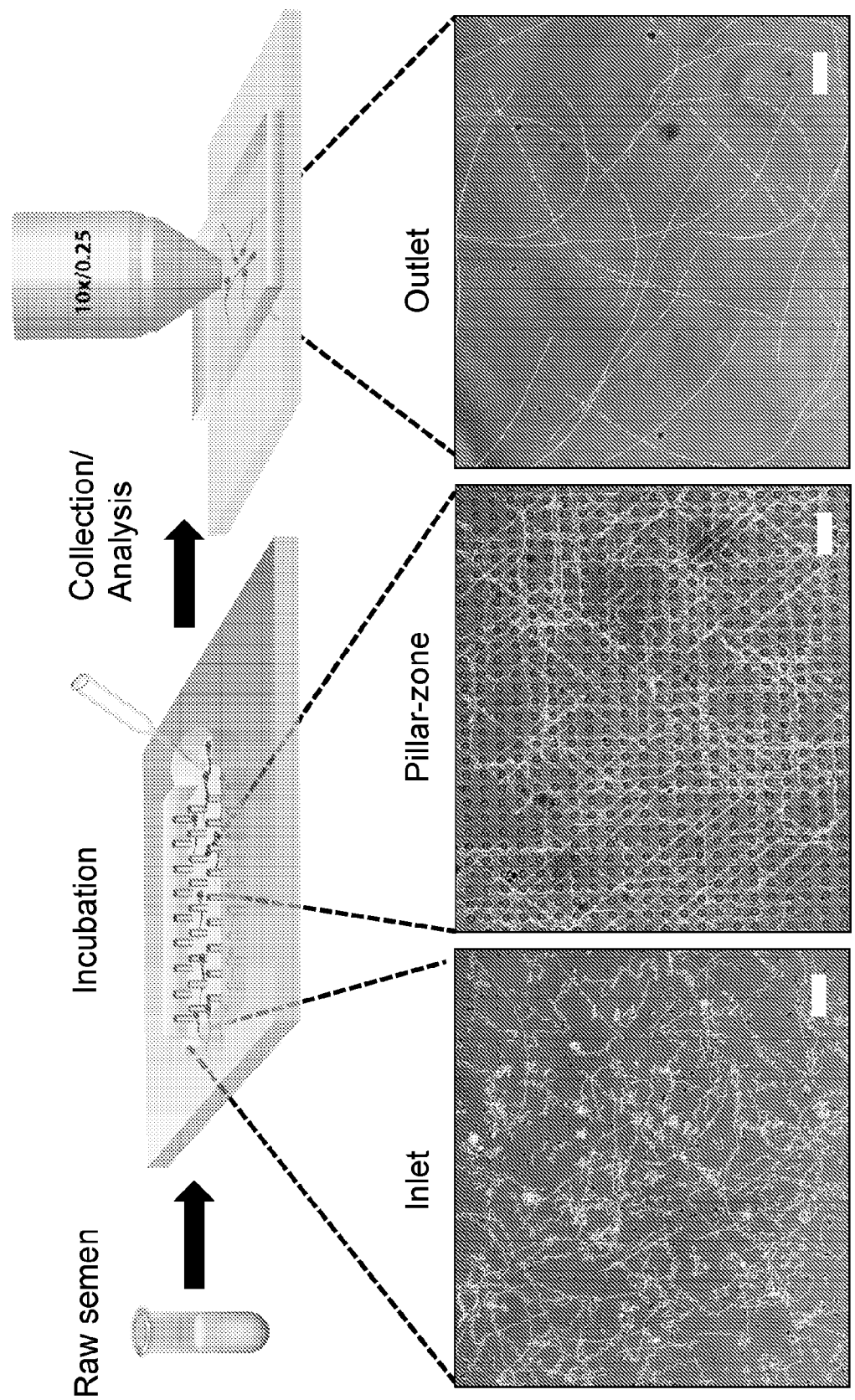
FIG. 19 shows according to an exemplary embodiment of the invention an outline of the method for selecting highly motile sperm from a raw sample.
Figure 20:
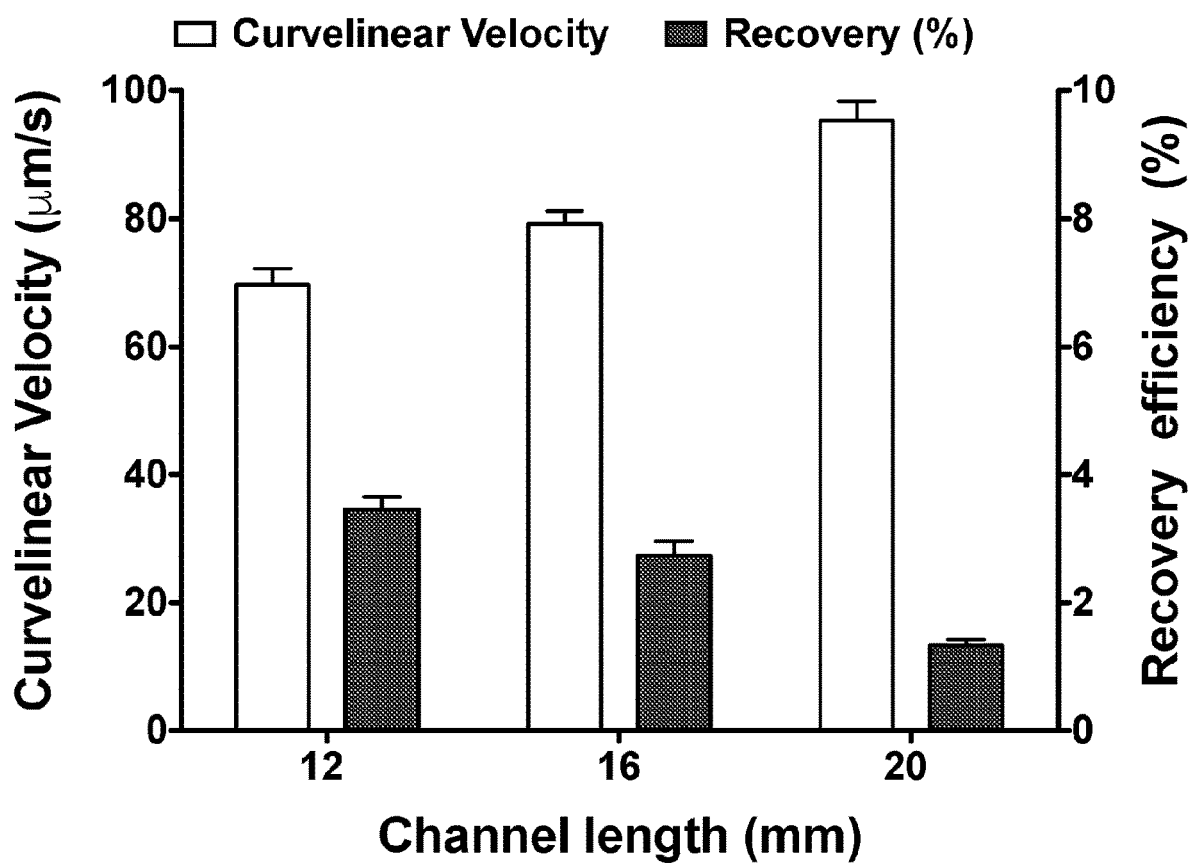
FIG. 20 shows according to an exemplary embodiment of the invention experimental results for the curvilinear velocity and sperm recovery rate of sperm after passing through a sample of exemplary channels with various lengths.
Figure 21:
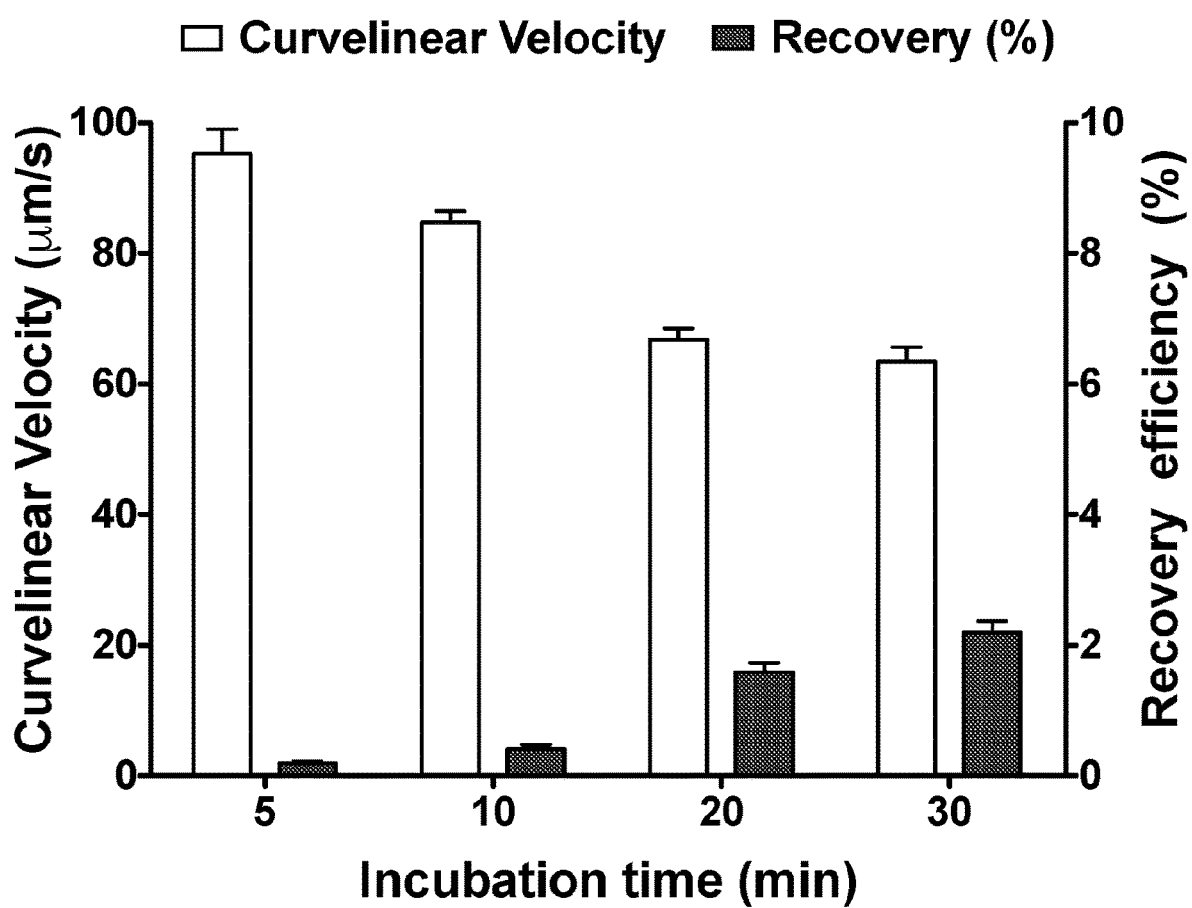
FIG. 21 shows according to an exemplary embodiment of the invention experimental results for the curvilinear velocity and sperm recovery rate of sperm after passing through a sample of exemplary channels with various incubation times.

FIG. 19 shows schematic illustrations of sperm sorting process: semen is initially loaded into the device, allowed to incubate, and then output sperm are recovered and analyzed, together with microscopy images of sperm trajectories at the inlet, the pillar-zone, and at the outlet. FIG. 20 shows experimental measurements of VCL on sperm recovery efficiency of SPARTAN chip with varying channel length. FIG. 21 shows experimental measurements of VCL on sperm recovery efficiency of SPARTAN chip with varying incubation time.

Figure 22:
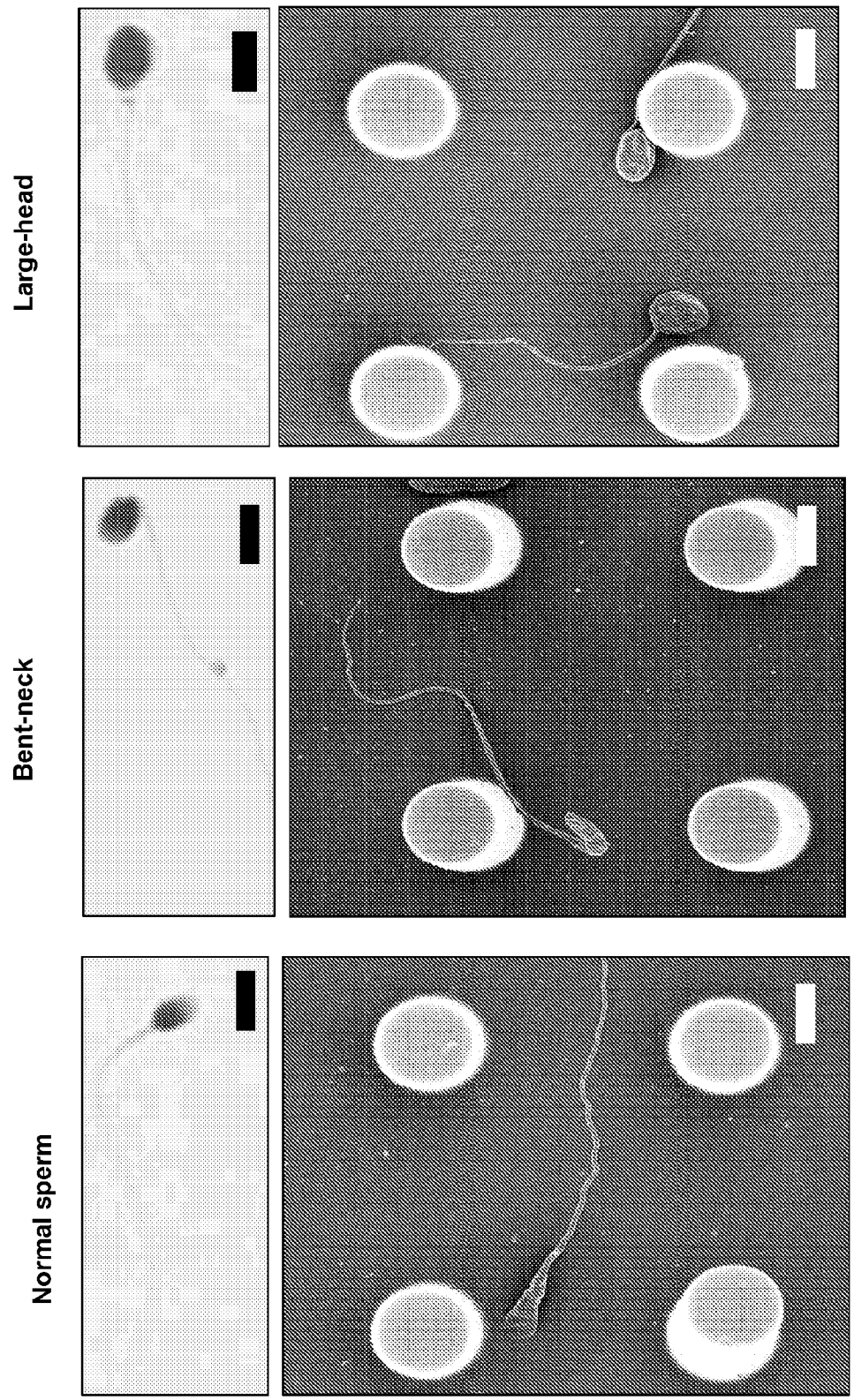
FIG. 22 shows according to an exemplary embodiment of the invention microscope and FESEM images of sperm with and without morphological defects in an exemplary embodiment of the device.
Figure 23:
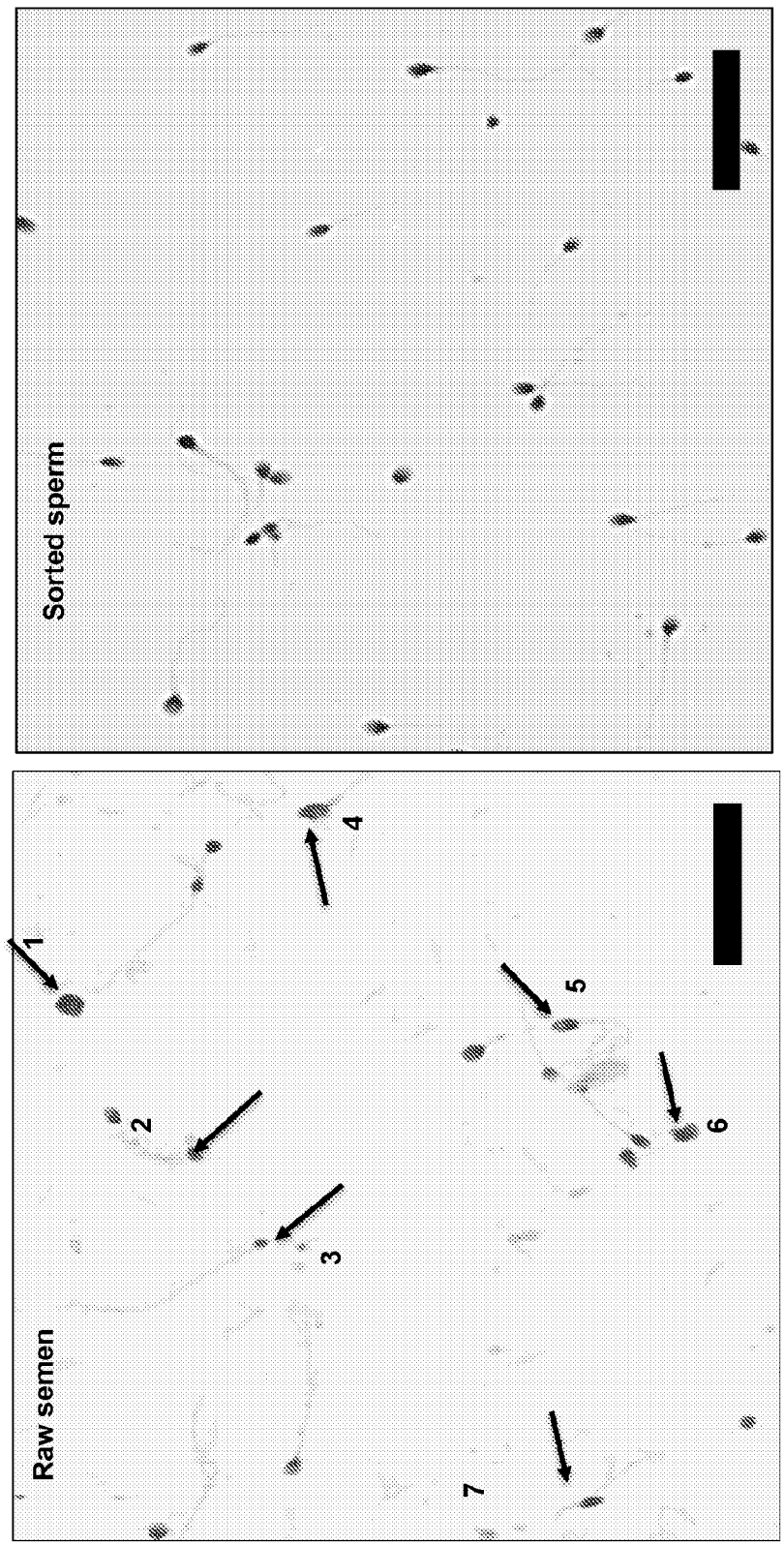
FIG. 23 shows according to an exemplary embodiment of the invention the difference in prevalence of sperm with morphological defects in a sperm sample before and after processing with an exemplary embodiment of the device.
Figure 24:
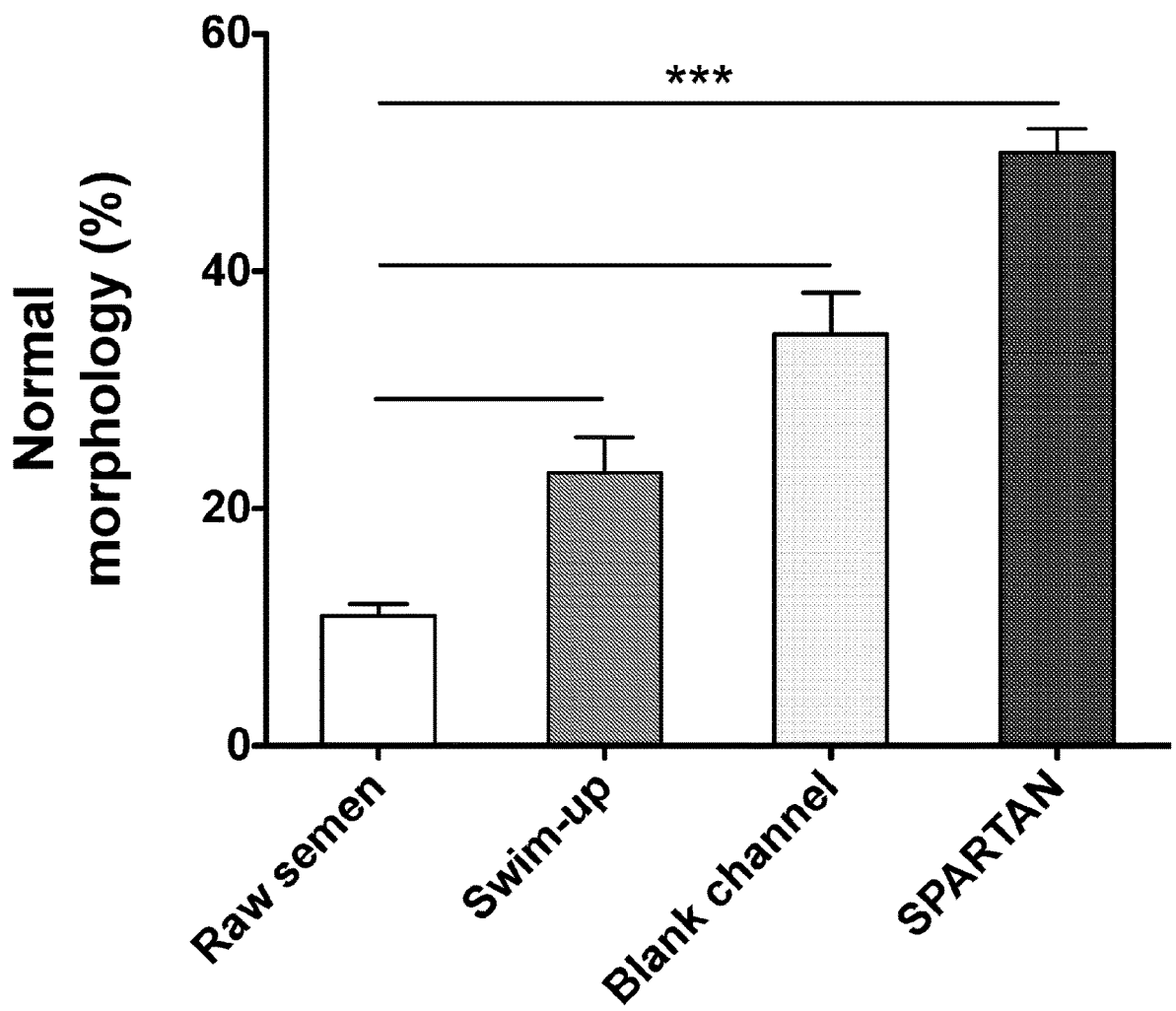
FIG. 24 shows according to an exemplary embodiment of the invention the percentage of sperm with normal morphology after processing with various methods, including with an exemplary embodiment of the device.

FIG. 22 shows microscopy images of Diff-Quick stained sperm and FESEM image with different morphological defects, (i) normal, (ii) bent-neck and (iii) large-head (scale bar 10 μm). FIG. 23 shows raw semen (arrows show the abnormal sperm), and sperm sorted using the SPARTAN chip (scale bar 50 μm). FIG. 24 shows SK morphology analysis of sperm processed through swim-up technique, blank and SPARTAN chips. Together, these results show how the device is capable of filtering sperm with morphological defects.

Figure 25:
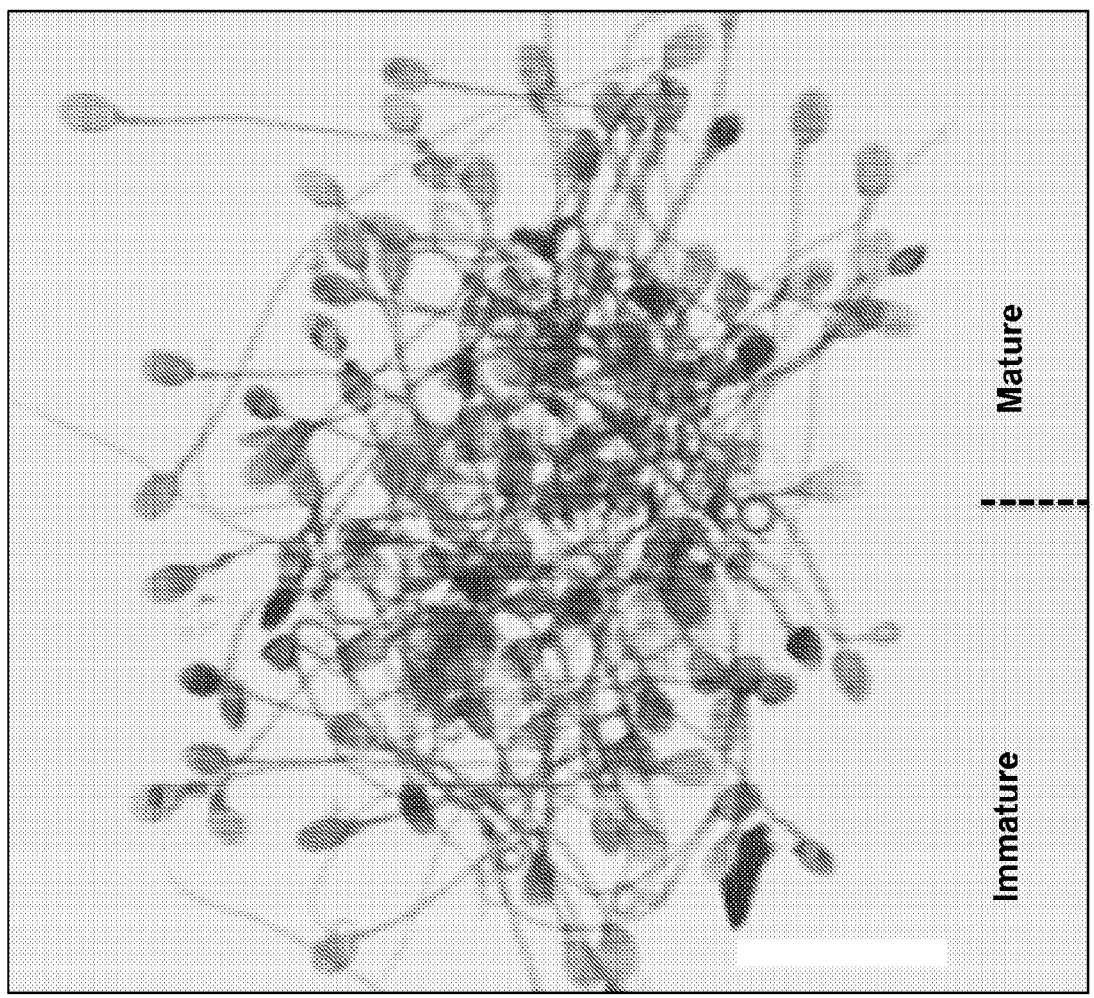
FIG. 25 shows according to an exemplary embodiment of the invention sperm maturity.
Figure 26:
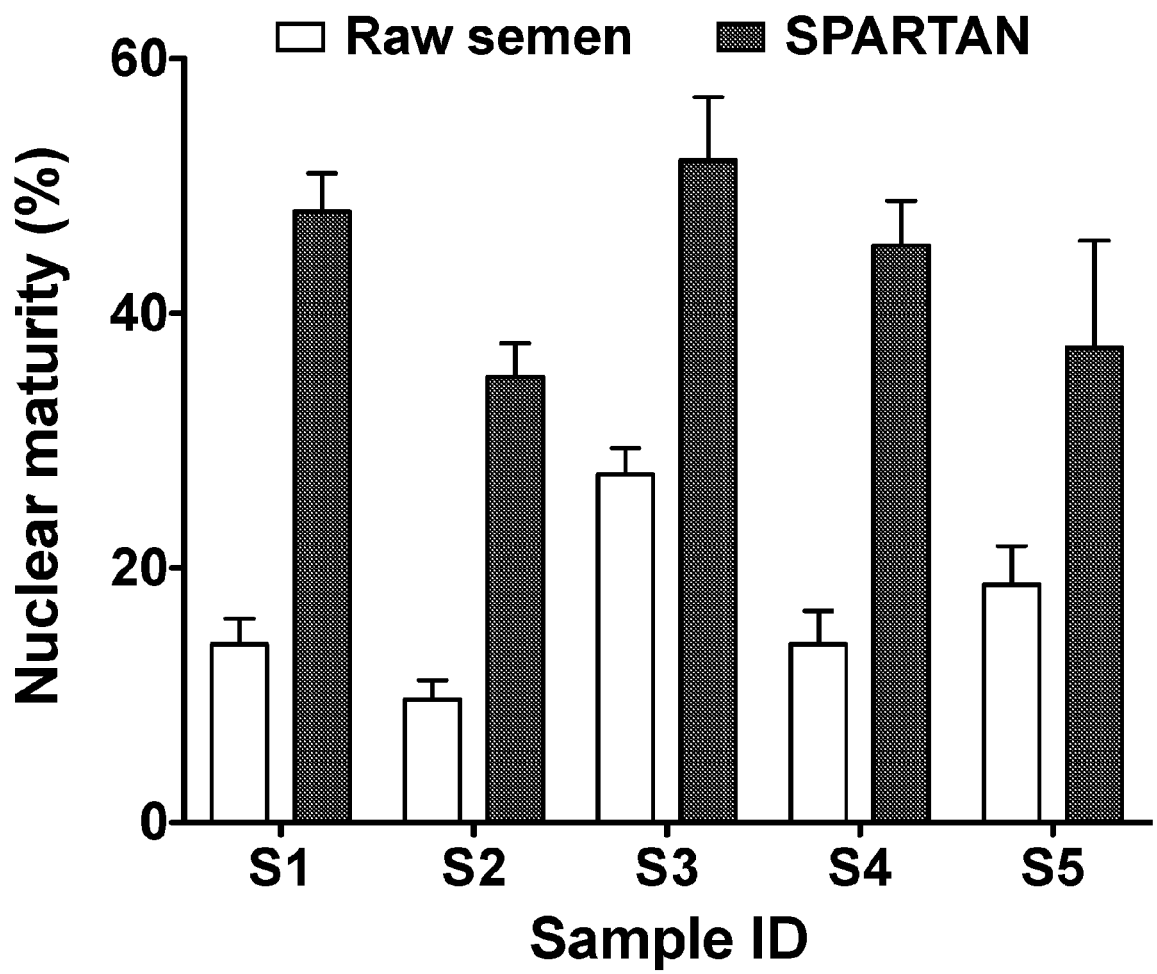
FIG. 26 shows according to an exemplary embodiment of the invention the difference in nuclear maturity of sperm in a sperm sample before and after processing with an exemplary embodiment of the device.
Figure 27:
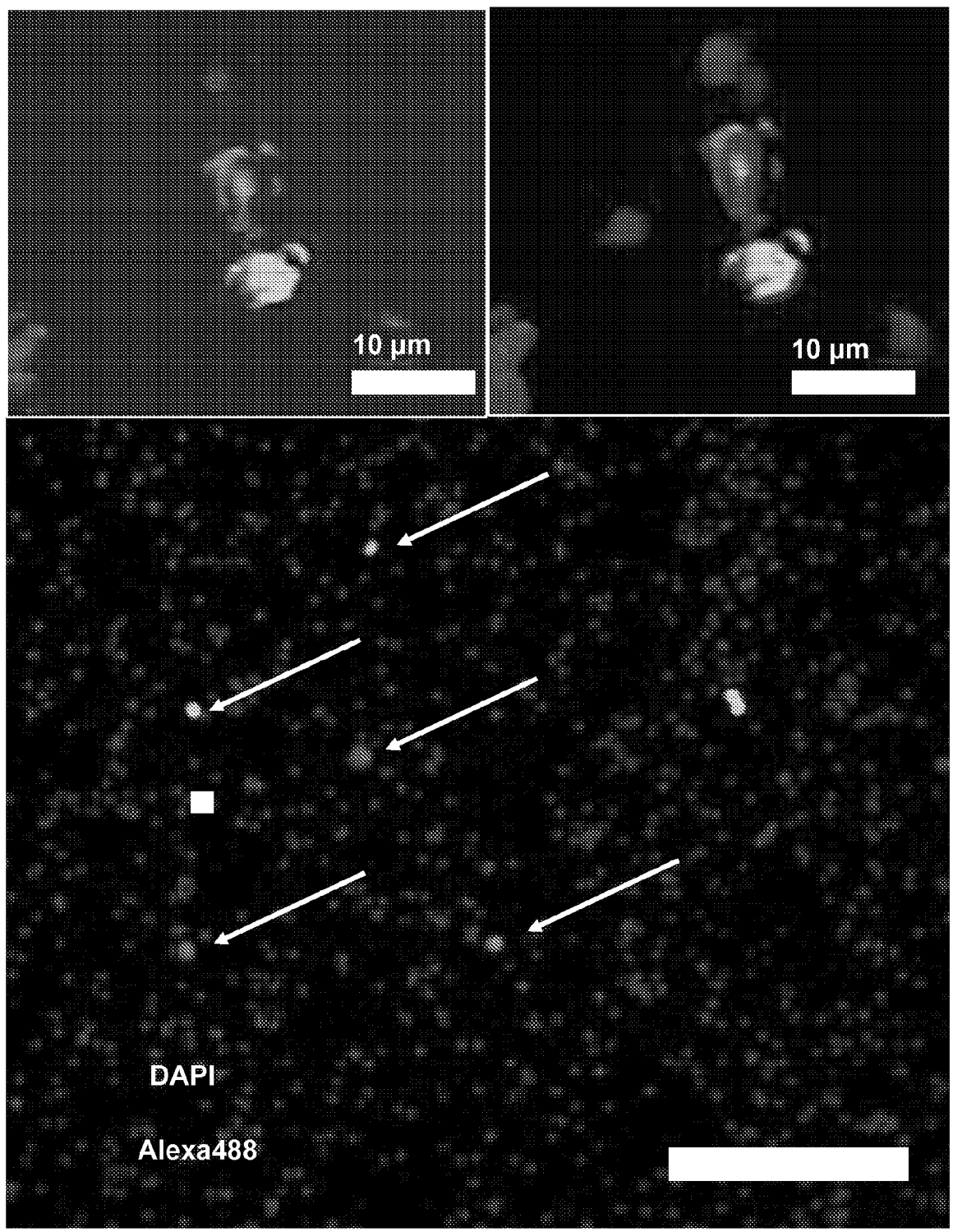
FIG. 27 shows according to an exemplary embodiment of the invention images of DNA fragmentation in sperm.
Figure 28:
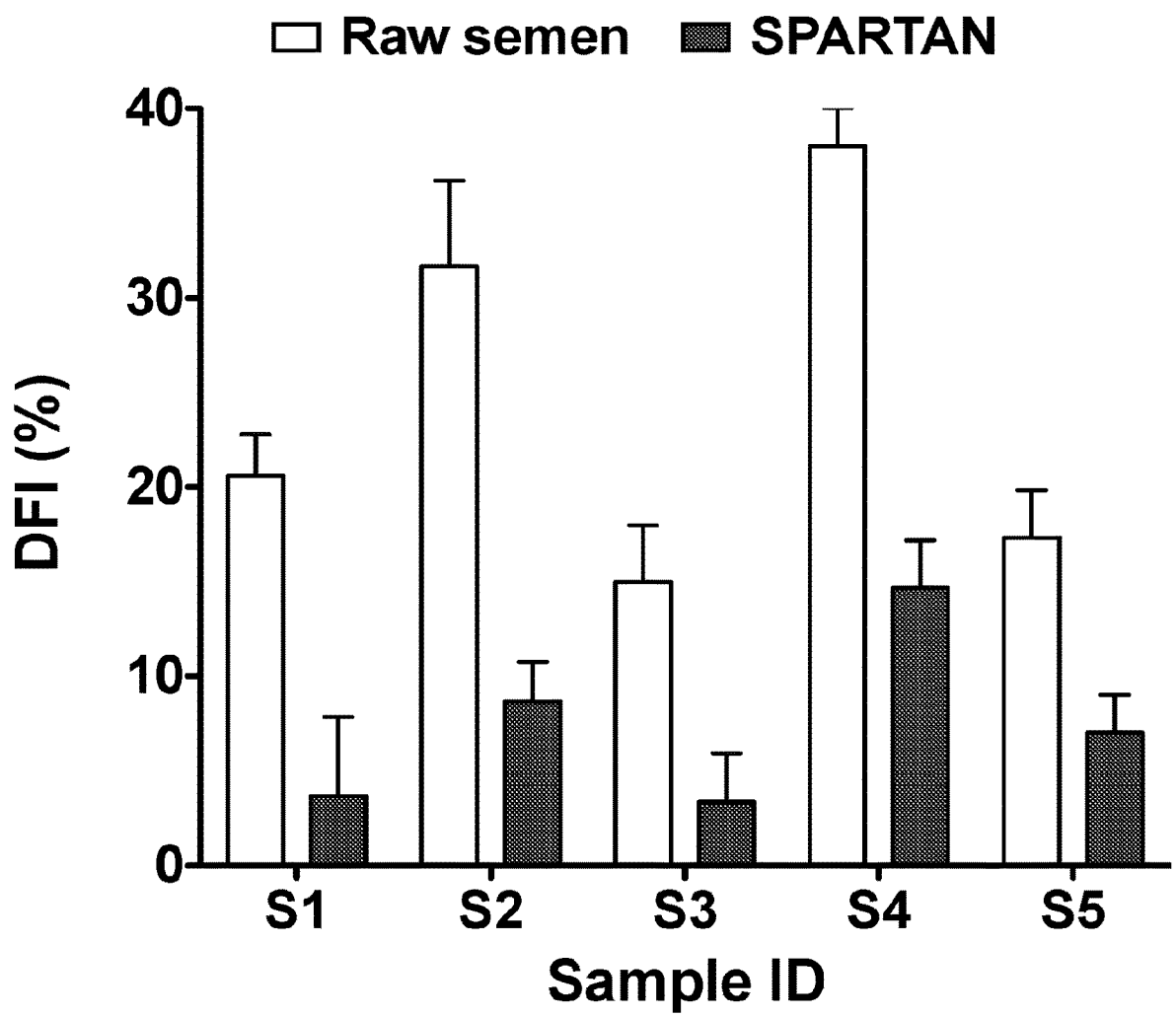
FIG. 28 shows according to an exemplary embodiment of the invention the difference in DFI of sperm in a sperm sample before and after processing with an exemplary embodiment of the device.
Figure 29:
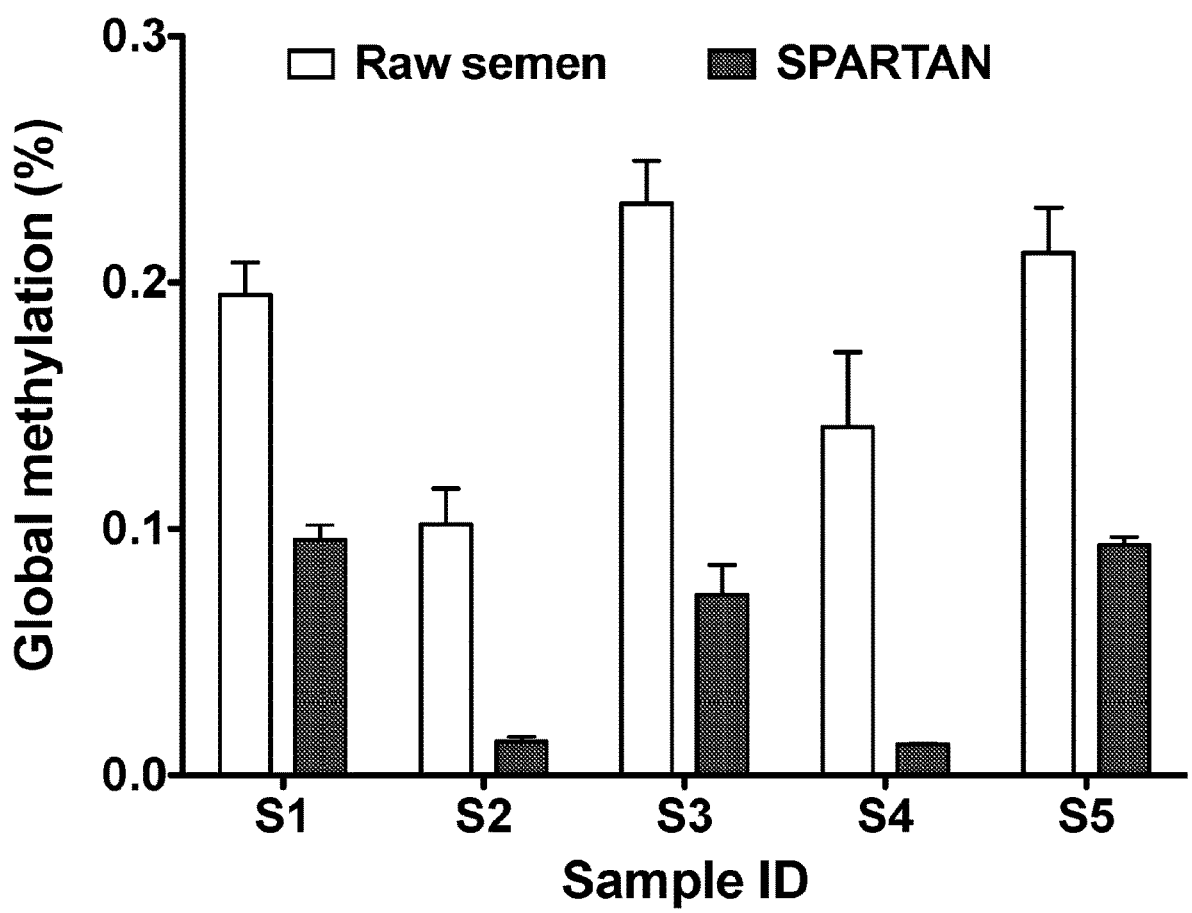
FIG. 29 shows according to an exemplary embodiment of the invention the difference in global methylation of sperm in a sperm sample before and after processing with an exemplary embodiment of the device.

FIG. 25 shows microscopy image of acidic aniline blue staining shows different stages of nuclear maturity of sperm. FIG. 26 shows analysis of nuclear maturity percentage of sperm sorted using the SPARTAN chip compared with those from a raw semen sample (n=5 semen samples). FIG. 27 shows fluorescently stained images from analysis of sperm DNA fragmentation using the TUNNEL assay. FIG. 28 shows analysis of DNA fragmentation index (DFI) of sperm sorted by SPARTAN chip compared with those from a raw semen sample (n=5 semen samples). FIG. 29 shows global methylation analysis of unsorted and sperm sorted by SPARTAN method.

Additional Notes

Sperm cells move faster within the periodic structures, similar to a self-induced flow field. One novelty of the system is that the structures that are periodically placed inside the channel change the way the sperm move. For instance, sperm with deformed morphologies interact and follow different pathways than the sperm with normal morphology. This is facilitated by the hydrodynamic interactions between the sperm and the periodic structures. The sperm cells are observed to move faster—in comparison to their counterparts in the inlet or outlet—within the pillar geometry due to effects including hydrodynamic interactions, and can be thought of as a self-induced flow field generated by the sperm cells. It is not obvious that sperm cells would actually interact with the periodic impediments in the channel in such a way as to preferably choose narrower paths. There is evidence of links between the genetic and epigenetic quality of the sperm and their morphology and motility, hence affecting its function. The net effect of these geometric structures, therefore, is to sort for functional sperm, which is unique and not an obvious outcome.

We also see in certain periodicities that the sperm cells move faster in the periodic impediment areas of the channel than outside. Depending on the geometry of the channel impediments, and the sperm tail movement and sperm morphology, this effect can be harnessed to more effectively sort sperm cells. Computer simulations are being used to develop the optimum designs, and have been used to guide initial experiments and the development of prototypes. This is an effect that is unique and was not expected. A naïve expectation would be that these periodic impediments would slow down sperm cells as they move through; however, we find that sperm cells can be made to speed up or divert in different directions depending on the specifics of the geometry. This leads to an unexpected self-sorting phenomenon.

The fluidic channel used in this invention is without movement or flow, and the fluid inside is not actively driven. The entire process of sorting happens without any external flow or attitudinal forces from the channel. The source of motion of the sperm cells is due their own motility, which has a unique pattern and varies from sperm to sperm, especially in morphologically challenged or clinically problematic samples. This unique self-induced movement of the sperm leads to the self-sorting behavior, which has never been reported before in the presence of periodic structures. This is especially striking given that we can alter the sorting effects by tuning the periodicity and shape of the impediments that we place in front of the sperm. These properties can be changed between different groups of rows and/or columns in order to induce specific sorting capabilities.

An exemplary range for the periodicities is, as we have observed in our computer simulations, that these effects that enable sorting are pronounced for periodicity spacing values in the range from one to five hundred micrometers.

Dimensions of Self-Sorting Device

In exemplary devices, the dimensions of the self-sorting device and the periodically spaced array of structures could be as follows:

Width or length spacing between pillars in the array: 1-250 micrometers, 5-200 micrometers or 5-30 micrometers.

Height of pillars in an array: about 50 micrometers with a range of 20 to 80 micrometers.

Length of inlet: about 2 mm with a range of up to 4 mm.

Length of channel: about 4 mm with a range of up to 20 mm.

Length of outlet: about 2 mm with a range of up to 4 mm.

Details of Modeling

An approach was used combining the strengths of the detail of the behavior captured by fine-grained simulations, along with the computational efficiency of coarse-grained models. We start off by characterizing the microscopic behavior of sperm in the specific geometry under consideration. Once we have enough data about the movement of the sperm in this geometry, we can use that information to rapidly extrapolate larger trajectories, allowing us to examine their mass behavior over long times.

Fine-grained Sperm Model: We model sperm as a bead-spring chain using a Hookean potential to prevent stretching and bending. Non-straight bonds are accomplished by rotating the second of the segments making up a bond by the desired angle of minimum energy for that bond [14].

Solvent Model: Sperm is coupled to a mesoscale solvent simulated using a technique known as Stochastic Rotation Dynamics (SRD). This technique models the fluid as a set of point particles, proceeding in discrete time steps, with each time step consisting of two processes. In the first (streaming) step, the particles move balistically, while in the second (collision) step, the particles exchange momentum with their local neighbors in a single collective collision [15-18].

To couple the sperm model to this solvent, the sperm's beads are included in the collective collisions, allowing them to exchange momentum with the fluid. This coupling is also used to insert the periodic structure array into the simulation. The array structures consist of particles that are confined to not be able to move. Additionally, the beads of the sperm and those of the obstacle interact with a truncated Lennard-Jones potential, providing a rigid repulsive interaction preventing the sperm from crossing the obstacle, and supplementing the hydrodynamic interactions mediated by the SRD fluid. [14] As the SRD solvent has a number of properties, including viscosity, that depend on temperature, it is necessary to ensure that the overall temperature of the system is constant over time. To achieve this, a thermostat process is inserted into the collision step [19]. All the parameters of the model are shown in FIG. 30.

Coarse-grained Lattice Model: To model a large number of sperm moving across a long time-period, we developed a coarse-grained model for the movement of the sperm through a lattice. This model considered that there are a finite number of directions that a sperm can be facing as it travels through the grid, and that its movement will depend on direction. At every step, there is a probability that the sperm will turn left or right, switching its state to the next one. This is represented by a Markov model of the directional state of the sperm. As a function of state, there is also a probability that the sperm will move in one of the cardinal directions.

Figure 32:
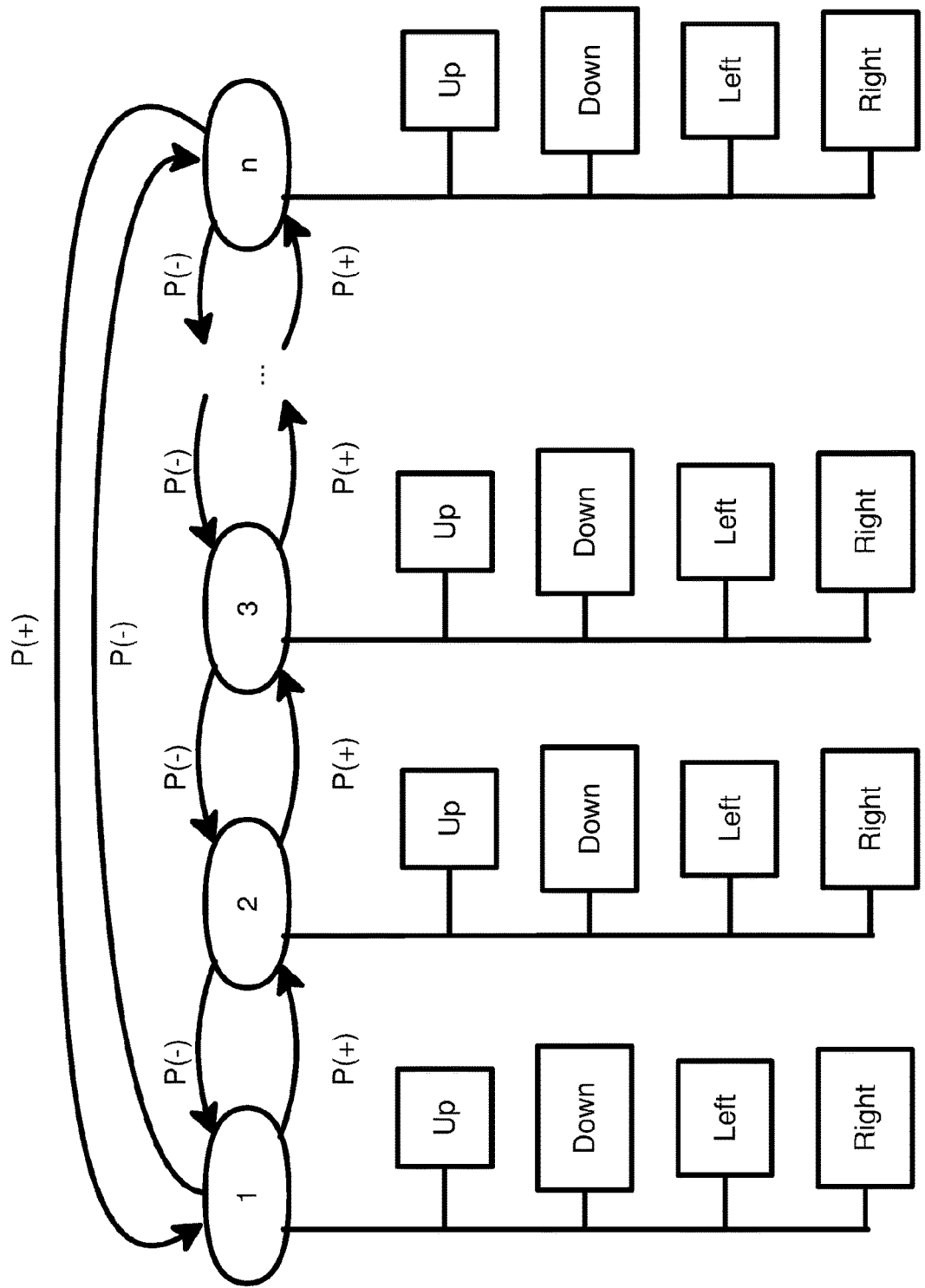
FIG. 32 shows according to an exemplary embodiment of the invention the relation of states that form the coarse-grained simulation of the device and method.

We label the movement probability as P(i, d) and the rotation probability as Q(e,d), where i is the directions {left, up, right, down}, d is the direction the sperm is currently facing, and e is the direction it will face next. State evolution consists of two parts, as shown mathematically in FIG. 31 and graphically in FIG. 32. The movement and rotation steps are alternated to advance the sperm's position and directional facing through time.

Transition between models: The SRD simulations produce trajectories of the sperm (as defined by the center of mass of the head), as well as its angle (defined as the vector connecting the center of mass of the head and the attachment point of the neck), as a function of time. This data is in units of the SRD parameters. The lattice model, however, requires units of pillars and tail-cycles. To convert this, the position data is first coarse-grained into integer coordinates on a grid defined by the pillars. Time is discretized doing a block average to one point per swimming cycle. In order to limit the amount of computation required to determine movement probabilities, the symmetry of the system is used to count every trajectory both as itself and as if it was rotated 180 degrees. In other words, a trajectory in which the sperm starts out facing left, and then goes up is equivalent to one in which it starts out facing right and then goes down.

The lattice model does not directly use trajectories however; it needs the transition probabilities for, at each step, the sperm moving and turning. To categorize the different directions that the sperm can face, a histogram of the distribution of angles is created, and its minima are used to separate out categories. Each category forms a discrete facing that the sperm can adopt in the lattice model. This coarse-grained trajectory is then used to calculate the movement and rotational transition probabilities. At every step, it is recorded if the sperm switches angle category or lattice position. Each category's results are averaged across every step taken by every sperm, to get a final array of probabilities. These probabilities are then used to feed the lattice model.

Figure 33:
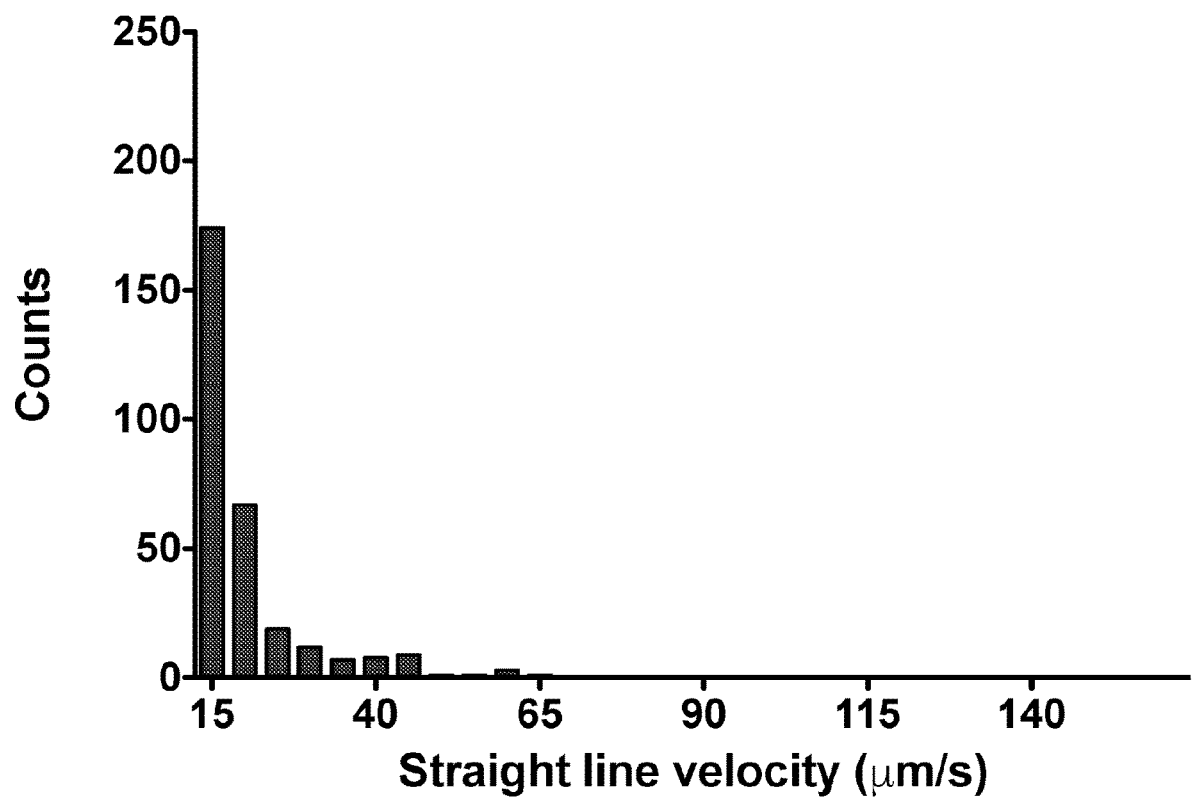
FIG. 33 shows according to an exemplary embodiment of the invention the distribution of VSLs used to simulate the device and method.

First, the sperm swimming speed is calibrated against the experimental results. This is done using the initial SRD results, by measuring the VSL and VCL of the simulated sperm cell in the SRD units. The pillar spacing establishes a conversion between SRD and physical length units, and the SRD parameter for the tail waveform a conversion between SRD units and tail cycles. For each sperm in the lattice simulation tests, its target velocity is drawn from the velocity distribution measured experimentally as shown in FIG. 33. This velocity is multiplied by the incubation time of that test, to get a total effective distance. This total path length is then multiplied by the micrometers to tail cycle conversion factor, to get a total number of tail cycles—each of which corresponds to a lattice simulation step—for that sperm. At this point, the simulation can proceed by taking that number of steps as described previously. At every step, the position of the sperm is recorded, and the final positions are used to determine which sperms reach the output and are collected, and which are not. For the ones that are collected, their velocity is recorded, and all are averaged to produce the overall results.

REFERENCES

[1] Ombelet, W., et al., *Infertility and the provision of infertility medical services in developing countries.* Human Reproduction Update, 2008. 14(6): p. 605-621.
[2] Turchi, P., *Prevalence, Definition, and Classification of Infertility*, in *Clinical Management of Male Infertility*. 2015, Springer. p. 5-11.
[3] Tasoglu, S., et al., *Exhaustion of Racing Sperm in Nature-Mimicking Microfluidic Channels During Sorting.* Small, 2013. 9(20): p. 3374-3384.
[4] Manipalviratn, S., A. DeCherney, and J. Segars, *Imprinting disorders and assisted reproductive technology.* Fertility and sterility, 2009. 91(2): p. 305-315.
[5] Maher, E. R., M. Afnan, and C. L. Barratt, *Epigenetic risks related to assisted reproductive technologies: epigenetics, imprinting, ART and icebergs?* Human Reproduction, 2003. 18(12): p. 2508-2511.
[6] Belva, F., et al., *Semen quality of young adult ICSI offspring: the first results.* Human Reproduction, 2016.
[7] Henkel, R. R. and W.-B. Schill, *Sperm preparation for ART.* Reprod Biol Endocrinol, 2003. 1(1): p. 108.
[8] Mortimer, D. and S. Mortimer, *Methods of sperm preparation for assisted reproduction.* Annals of the Academy of Medicine, Singapore, 1992. 21(4): p. 517-524.
[9] Asghar, W., et al., *Selection of functional human sperm with higher DNA integrity and fewer reactive oxygen species.* Advanced healthcare materials, 2014. 3(10): p. 1671-1679.
[10] Berkovitz, A., et al., *How to improve IVF-ICSI outcome by sperm selection.* Reproductive biomedicine online, 2006. 12(5): p. 634-638.
[11] Sivanarayana, T., et al., *Sperm DNA fragmentation assay by sperm chromatin dispersion (SCD): correlation between DNA fragmentation and outcome of intracytoplasmic sperm injection.* Reproductive Medicine and Biology, 2014. 13(2): p. 87-94.
[12] Dariš, B., et al., *Sperm morphological abnormalities as indicators of DNA fragmentation and fertilization in ICSI.* Archives of gynecology and obstetrics, 2010. 281(2): p. 363-367.
[13] Mohammad, H. N.-E., et al., *Effect of sperm DNA damage and sperm protamine deficiency on fertilization and embryo development post-ICSI.* Reproductive biomedicine online, 2005. 11(2): p. 198-205.
[14] Y. Yang, J. Elgeti, and G. Gompper. *Phys Rev E* 78, 061903 (2008).
[15] Malevanets and R. Kapral. *J Chem Phys* 110, 8605-8613 (1999).
[16] E. Tüzel, M. Strauss, T. Ihle, and D. M. Kroll. *Phys Rev E* 68, 036701 (2003).
[17] E. Tüzel, T. Ihle, and D. M. Kroll. *Phys Rev E* 74, 056702 (2006).
[18] E. Tüzel, Ph.D. Thesis, University of Minnesota (2006).
[19] H. Hijar and G. Sutmann. *Physical Review E* 83 046708 (2011).

What is claimed is:

1. A method of self-sorting motile, morphologically-normal sperm cells with high DNA integrity from raw or unprocessed semen, comprising:
   a) providing a fluidic channel with an inlet at one end and an outlet at the other end,
wherein an array of pillar-structures is periodically spaced inside the fluidic channel, wherein the spacing between adjacent pillar-structures ranges from one micrometer to 250 micrometers;
   b) introducing raw or unprocessed semen containing sperm cells at the inlet of the fluidic channel;
   c) self-sorting the sperm cells by their own self-induced movements within the fluidic channel through their interactions with the periodically spaced array of pillar-structures and without the use of any external flow, forces or mechanisms to feed the raw or unprocessed sperm through the fluidic channel; and
   d) collecting at the outlet sorted sperm cells from the fluidic channel, and
wherein the sorted sperm cells are the motile, morphologically-normal sperm cells with high DNA integrity compared to the raw or unprocessed semen.

2. The method of claim 1, wherein a length of the fluidic channel ranges from 4 mm to 20 mm, and wherein a height of the pillar-structures ranges from 20 μm to 80 μm.

3. The method of claim 1, wherein the spacing between adjacent pillar-structures ranges from 5 μm to 200 μm.

4. The method of claim 1, wherein the spacing between adjacent pillar-structures ranges from 5 μm to 30 μm.

5. The method of claim 1, wherein the spacing between adjacent pillar-structures ranges from 18 μm to 30 μm in a first direction.

6. The method of claim 1, wherein the length of the fluidic channel ranges from 12 mm to 20 mm.

7. The method of claim 1, wherein the width of the fluidic channel is 1.5 mm.

8. The method of claim 1, wherein allowing the sperm cells in the sample to move from the inlet, through the array and to the outlet comprises incubating for a period of time ranging from 5 minutes to 30 minutes.

9. The method of claim 1, wherein the array of pillar-structures has a periodicity of 18×26 μm, 22×22 μm, 22×26 μm, 26×26 μm or 30×26 μm.

10. The method of claim 5, wherein the spacing between adjacent pillar-structures ranges from 22 μm to 26 μm in a second direction.

* * * * *

UNITED STATES PATENT AND TRADEMARK OFFICE
CERTIFICATE OF CORRECTION

PATENT NO. : 11,618,882 B2
APPLICATION NO. : 16/070368
DATED : April 4, 2023
INVENTOR(S) : Utkan Demirci et al.

It is certified that error appears in the above-identified patent and that said Letters Patent is hereby corrected as shown below:

In the Specification

Column 3, Line 43, "30>26" should be --30×26--.

Signed and Sealed this
Eighth Day of August, 2023

Katherine Kelly Vidal
*Director of the United States Patent and Trademark Office*